United States Patent
Xu et al.

(10) Patent No.: US 10,624,974 B2
(45) Date of Patent: Apr. 21, 2020

(54) ANTI-OX40 ANTIBODY AND APPLICATION THEREOF

(71) Applicant: Dingfu Biotarget Co., Ltd., Suzhou, Jiangsu (CN)

(72) Inventors: Ting Xu, Jiangsu (CN); Yan Luan, Jiangsu (CN); Xiaoxiao Wang, Jiangsu (CN); Jianjian Peng, Jiangsu (CN); Shuli Ma, Jiangsu (CN); Hui Ma, Jiangsu (CN); Xiaolong Pan, Jiangsu (CN); Shilong Fu, Jiangsu (CN); Shanshan Ning, Jiangsu (CN); Yeqiong Fei, Jiangsu (CN); Meng Zhao, Jiangsu (CN)

(73) Assignee: Dingfu Biotarget Co., Ltd., Suzhou, Jiangsu (CN)

( * ) Notice: Subject to any disclaimer, the term of this patent is extended or adjusted under 35 U.S.C. 154(b) by 80 days.

(21) Appl. No.: 15/768,242

(22) PCT Filed: Oct. 15, 2015

(86) PCT No.: PCT/CN2015/091958
§ 371 (c)(1),
(2) Date: Apr. 13, 2018

(87) PCT Pub. No.: WO2017/063162
PCT Pub. Date: Apr. 20, 2017

(65) Prior Publication Data
US 2018/0339059 A1    Nov. 29, 2018

(51) Int. Cl.
| | | |
|---|---|---|
| *C07K 16/28* | (2006.01) | |
| *A61K 39/395* | (2006.01) | |
| *A61K 47/68* | (2017.01) | |
| *C12N 15/63* | (2006.01) | |
| *A61P 35/00* | (2006.01) | |
| *C07H 21/04* | (2006.01) | |
| *C07K 16/30* | (2006.01) | |
| *C12N 5/07* | (2010.01) | |
| *A61K 39/00* | (2006.01) | |

(52) U.S. Cl.
CPC ...... *A61K 47/6851* (2017.08); *A61K 39/3955* (2013.01); *A61P 35/00* (2018.01); *C07H 21/04* (2013.01); *C07K 16/2878* (2013.01); *C07K 16/30* (2013.01); *C12N 5/06* (2013.01); *C12N 15/63* (2013.01); *A61K 2039/505* (2013.01); *C07K 2317/21* (2013.01); *C07K 2317/33* (2013.01); *C07K 2317/565* (2013.01); *C07K 2317/622* (2013.01); *C07K 2317/75* (2013.01); *C07K 2317/90* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | | |
|---|---|---|---|---|
| 2010/0136030 A1* | 6/2010 | Salah-Eddine | .... | C07K 16/2878 424/173.1 |
| 2015/0307617 A1* | 10/2015 | Du | ...... | A61K 47/6849 424/133.1 |
| 2016/0347847 A1 | 12/2016 | Van Dijk et al. | | |
| 2016/0347849 A1 | 12/2016 | Cai et al. | | |

FOREIGN PATENT DOCUMENTS

| | | |
|---|---|---|
| CN | 103221427 A | 7/2013 |
| CN | 103717263 A | 4/2014 |
| CN | 104080809 A | 10/2014 |
| JP | 2011-505836 A | 3/2011 |
| JP | 2013-538057 A | 10/2013 |
| JP | 2014-527814 A | 10/2014 |
| WO | 03106498 A | 12/2003 |
| WO | 2009/079335 A | 6/2009 |
| WO | 2012027328 A | 3/2012 |
| WO | 2014148895 A | 9/2014 |
| WO | 2015153513 A | 10/2015 |
| WO | 2016057667 A | 4/2016 |

OTHER PUBLICATIONS

Compaan, et al., The Crystal Structure of the Costimulatory OX40-OX40L Complex, Structure, Aug. 2006, vol. 14.
Curti, et al., OX40 Is a Potent Immune-Stimulating Target in Late-Stage Cancer Patients, Cancer Research, Oct. 31, 2013.
Godfrey, et al., Identification of a human OX-40 Ligand, a Costimulator of CD 4+ T cells with Homology to Tumor Necrosis Factor, J.Exp.Med., Aug. 1, 1994, vol. 180.
Gough, et al., Adjuvant Therapy With Agonistic Antibodies to CD134 (OX40) Increases Local Control After Surgical or Radiation Therapy of Cancer in Mice, J Immunother., Oct. 2010, vol. 30.
Linch, et al., OX40 agonists and combination immunotherapy: putting the pedal to the metal, Frontiers in Oncology, Feb. 16, 2015, vol. 5.
Palucka, et al., Boosting Vaccinations with Peptide-Pulsed CD34+ Progenitor-Derived Dendritic Cells Can Expand Long-Lived Melanoma Peptide-Specific CD8+ T Cells in Patients with Metastatic Melanoma, J Immunother., Mar. 2005, vol. 28.

(Continued)

*Primary Examiner* — Laura B Goddard
(74) *Attorney, Agent, or Firm* — Honigman LLP; Thomas A. Wootton, Esq.; Jonathan P. O'Brien

(57) ABSTRACT

The present application provides an anti-OX40 human antibody. In particular, a human antibody specifically binding to OX40 is obtained with yeast display screening, and the affinity of the antibody is improved with affinity maturation. The present application also provides a use of the antibody for the prevention or treatment of tumors.

6 Claims, 14 Drawing Sheets

Specification includes a Sequence Listing.

(56) References Cited

OTHER PUBLICATIONS

Paterson, et al., Antigens of Activated Rat T Lymphocytes Including a Molecule of 50,000 M, Detected Only on CD4 Positive T Blasts, Molecular Immunology., Jun. 9, 1987, vol. 24, No. 12.
International Search Report of WO 2017063162 (PCT/CN2015/091958) dated Jul. 14, 2016.

* cited by examiner

OX40-21

OX40-21-1

OX40-21-2

OX40-21-7

OX40-21-11

OX40-21-13

OX40-21-14

OX40-21-16

OX40-21-17

SEQUENCE LISTING

<160> NUMBER OF SEQ ID NOS: 80

<210> SEQ ID NO 1
<211> LENGTH: 15
<212> TYPE: PRT
<213> ORGANISM: Homo sapiens

<400> SEQUENCE: 1

Gly Gly Gly Gly Ser Gly Gly Gly Gly Ser Gly Gly Gly Gly Ser
1               5                   10                  15

<210> SEQ ID NO 2
<211> LENGTH: 22
<212> TYPE: DNA
<213> ORGANISM: Artificial Sequence
<220> FEATURE:
<223> OTHER INFORMATION: PCR primer

<400> SEQUENCE: 2
cgtagaatcg agaccgagga ga                                              22

<210> SEQ ID NO 3
<211> LENGTH: 23
<212> TYPE: DNA
<213> ORGANISM: Artificial Sequence
<220> FEATURE:
<223> OTHER INFORMATION: PCR primer

<400> SEQUENCE: 3
ctggtggtgg tggttctgct agc                                             23

<210> SEQ ID NO 4
<211> LENGTH: 119
<212> TYPE: PRT
<213> ORGANISM: Homo sapiens

<400> SEQUENCE: 4

Gln Val Gln Leu Gln Gln Trp Gly Ala Gly Leu Leu Lys Pro Ser Glu
1               5                   10                  15

Thr Leu Ser Leu Thr Cys Gly Phe Asn Gly Glu Tyr Phe Thr Asp Tyr
            20                  25                  30

Phe Trp Thr Trp Val Arg Gln Pro Pro Gly Glu Ala Leu Glu Trp Leu
        35                  40                  45

Ala Leu Ile Tyr Trp Asp Asp Asp Glu Arg Tyr Ser Pro Ser Leu Lys
    50                  55                  60

Asn Arg Leu Ile Ile Thr Lys Asp Ile Ser Lys Asn Gln Val Val Leu
65                  70                  75                  80

Thr Met Thr His Met Glu Pro Ala Asp Thr Gly Thr Tyr Tyr Cys Ala
                85                  90                  95

Arg Trp Gly Gly Ser Leu Met Asn Ala Phe Asp Val Trp Gly Pro Gly
            100                 105                 110

Thr Met Val Thr Val Ser Ser
        115

<210> SEQ ID NO 5
<211> LENGTH: 5
<212> TYPE: PRT
<213> ORGANISM: Homo sapiens

<400> SEQUENCE: 5

Asp Tyr Phe Trp Thr
1               5

<210> SEQ ID NO 6
<211> LENGTH: 16
<212> TYPE: PRT
<213> ORGANISM: Homo sapiens

<400> SEQUENCE: 6

Leu Ile Tyr Trp Asp Asp Glu Arg Tyr Ser Pro Ser Leu Lys Asn
1               5                   10                  15

<210> SEQ ID NO 7
<211> LENGTH: 11
<212> TYPE: PRT
<213> ORGANISM: Homo sapiens

<400> SEQUENCE: 7

Trp Gly Gly Ser Leu Met Asn Ala Phe Asp Val
1               5                   10

<210> SEQ ID NO 8
<211> LENGTH: 30
<212> TYPE: PRT
<213> ORGANISM: Homo sapiens

<400> SEQUENCE: 8

Gln Val Gln Leu Gln Gln Trp Gly Ala Gly Leu Leu Lys Pro Ser Glu
1               5                   10                  15

Thr Leu Ser Leu Thr Cys Gly Phe Asn Gly Glu Tyr Phe Thr
            20                  25                  30

<210> SEQ ID NO 9
<211> LENGTH: 14
<212> TYPE: PRT
<213> ORGANISM: Homo sapiens

<400> SEQUENCE: 9

Trp Val Arg Gln Pro Pro Gly Glu Ala Leu Glu Trp Leu Ala
1               5                   10

<210> SEQ ID NO 10
<211> LENGTH: 32
<212> TYPE: PRT
<213> ORGANISM: Homo sapiens

<400> SEQUENCE: 10

Arg Leu Ile Ile Thr Lys Asp Ile Ser Lys Asn Gln Val Val Leu Thr
1               5                   10                  15

Met Thr His Met Glu Pro Ala Asp Thr Gly Thr Tyr Tyr Cys Ala Arg
            20                  25                  30

<210> SEQ ID NO 11
<211> LENGTH: 11
<212> TYPE: PRT
<213> ORGANISM: Homo sapiens

<400> SEQUENCE: 11

Trp Gly Pro Gly Thr Met Val Thr Val Ser Ser
1               5                   10

<210> SEQ ID NO 12
<211> LENGTH: 357
<212> TYPE: DNA
<213> ORGANISM: Artificial Sequence
<220> FEATURE:

<223> OTHER INFORMATION: PCR primer

<400> SEQUENCE: 12

| | | | | |
|---|---|---|---|---|
| caggtgcagc tacagcagtg gggcgcagga ctgttgaagc cttcggagac cctgtccctc | 60 |
| acctgcggtt tcaatggaga atacttcact gattacttct ggacctgggt ccggcagccc | 120 |
| cccggagagg ccctggagtg gcttgcactc atttattggg atgatgatga gcgctacagc | 180 |
| ccatctctga agaacagact catcatcacc aaggacattt ccaaaaacca ggtggtcctt | 240 |
| acaatgaccc acatggagcc tgcggacaca ggcacctatt actgtgcgag atggggtggt | 300 |
| tctttaatga acgcttttga tgtctggggc ccagggacaa tggtcaccgt ctcttca | 357 |

<210> SEQ ID NO 13
<211> LENGTH: 110
<212> TYPE: PRT
<213> ORGANISM: Homo sapiens

<400> SEQUENCE: 13

Gln Ser Ala Leu Ile Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Arg His Pro Gly Lys Ala Pro Arg Leu
        35                  40                  45

Met Ile Tyr Asp Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Ile Ala Val Phe Gly Gly Gly Thr Gln Leu Thr Val Leu
            100                 105                 110

<210> SEQ ID NO 14
<211> LENGTH: 14
<212> TYPE: PRT
<213> ORGANISM: Homo sapiens

<400> SEQUENCE: 14

Thr Gly Thr Ser Ser Asp Val Gly Gly Tyr Asn Tyr Val Ser
1               5                   10

<210> SEQ ID NO 15
<211> LENGTH: 7
<212> TYPE: PRT
<213> ORGANISM: Homo sapiens

<400> SEQUENCE: 15

Asp Val Thr Lys Arg Pro Ser
1               5

<210> SEQ ID NO 16
<211> LENGTH: 10
<212> TYPE: PRT
<213> ORGANISM: Homo sapiens

<400> SEQUENCE: 16

Ser Ser Tyr Thr Ser Ser Ser Ile Ala Val
1               5                   10

<210> SEQ ID NO 17
<211> LENGTH: 22
<212> TYPE: PRT
<213> ORGANISM: Homo sapiens

<400> SEQUENCE: 17

Gln Ser Ala Leu Ile Gln Pro Ala Ser Val Ser Gly Ser Pro Gly Gln
1               5                   10                  15

Ser Ile Thr Ile Ser Cys
            20

<210> SEQ ID NO 18
<211> LENGTH: 15
<212> TYPE: PRT
<213> ORGANISM: Homo sapiens

<400> SEQUENCE: 18

Trp Tyr Gln Arg His Pro Gly Lys Ala Pro Arg Leu Met Ile Tyr
1               5                   10                  15

<210> SEQ ID NO 19
<211> LENGTH: 32
<212> TYPE: PRT
<213> ORGANISM: Homo sapiens

<400> SEQUENCE: 19

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 20
<211> LENGTH: 10
<212> TYPE: PRT
<213> ORGANISM: Homo sapiens

<400> SEQUENCE: 20

Phe Gly Gly Gly Thr Gln Leu Thr Val Leu
1               5                   10

<210> SEQ ID NO 21
<211> LENGTH: 330
<212> TYPE: DNA
<213> ORGANISM: Artificial Sequence
<220> FEATURE:
<223> OTHER INFORMATION: PCR primer

<400> SEQUENCE: 21
cagtctgccc tgattcagcc tgcctccgtg tctgggtctc ctggacagtc gatcaccatc      60
tcctgcactg gaaccagtag tgacgttggt ggttataatt atgtctcctg gtaccaacga     120
cacccaggca agcccccag actcatgatt tatgatgtca ctaagcggcc ctcaggggtt      180
tctaatcgct tctctggctc caagtctggc aacacggcct ccctgaccat ctctgggctc     240
caggctgagg acgaggctga ttattactgc agctcatata aagcagcag cattgctgtg     300 ttcggaggag gcacccagct gaccgtcctc                                      330

<210> SEQ ID NO 22
<211> LENGTH: 133
<212> TYPE: PRT
<213> ORGANISM: Homo sapiens

<400> SEQUENCE: 22

Gln Val Gln Leu Val Glu Ser Glu Gly Gly Leu Val Gln Pro Gly Gly
1               5                   10                  15

Ser Leu Arg Leu Ser Cys Ala Ala Ser Arg Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Met Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Thr Leu Arg Ala Glu Asp Thr Ala Met Tyr Tyr Cys
            85                  90                  95

Thr Arg Val Ser Phe Gly Val Pro Thr Tyr Asp Asp Phe Trp Arg Ser
        100                 105                 110

Tyr Ala Thr Pro Ala Trp Tyr Phe Asp Phe Trp Gly Arg Gly Thr Leu
            115                 120                 125

Val Thr Val Ser Ser
            130

<210> SEQ ID NO 23
<211> LENGTH: 5
<212> TYPE: PRT
<213> ORGANISM: Homo sapiens

<400> SEQUENCE: 23

Asn Tyr Trp Met Ser
1               5

<210> SEQ ID NO 24
<211> LENGTH: 17
<212> TYPE: PRT
<213> ORGANISM: Homo sapiens

<400> SEQUENCE: 24

Asn Ile Lys Gln Asp Gly Ser Glu Lys Tyr Tyr Met Asp Ser Val Lys
1               5                   10                  15

Gly

<210> SEQ ID NO 25
<211> LENGTH: 24
<212> TYPE: PRT
<213> ORGANISM: Homo sapiens

<400> SEQUENCE: 25

Val Ser Phe Gly Val Pro Thr Tyr Asp Asp Phe Trp Arg Ser Tyr Ala
1               5                   10                  15

Thr Pro Ala Trp Tyr Phe Asp Phe
            20

<210> SEQ ID NO 26
<211> LENGTH: 30
<212> TYPE: PRT
<213> ORGANISM: Homo sapiens

<400> SEQUENCE: 26

Gln Val Gln Leu Val Glu Ser Glu Gly Gly Leu Val Gln Pro Gly Gly
1               5                   10                  15

Ser Leu Arg Leu Ser Cys Ala Ala Ser Arg Phe Thr Phe Ser
            20                  25                  30

<210> SEQ ID NO 27
<211> LENGTH: 14
<212> TYPE: PRT
<213> ORGANISM: Homo sapiens

<400> SEQUENCE: 27

Trp Val Arg Gln Ala Pro Gly Lys Gly Leu Glu Trp Val Ala
1               5                   10

<210> SEQ ID NO 28
<211> LENGTH: 32
<212> TYPE: PRT
<213> ORGANISM: Homo sapiens

<400> SEQUENCE: 28

Arg Phe Thr Ile Ser Arg Asp Asn Ala Lys Asn Ser Leu Phe Leu Gln
1               5                   10                  15

Met Asn Thr Leu Arg Ala Glu Asp Thr Ala Met Tyr Tyr Cys Thr Arg
            20                  25                  30

<210> SEQ ID NO 29
<211> LENGTH: 11
<212> TYPE: PRT
<213> ORGANISM: Homo sapiens

<400> SEQUENCE: 29

Trp Gly Arg Gly Thr Leu Val Thr Val Ser Ser
1               5                   10

<210> SEQ ID NO 30
<211> LENGTH: 399
<212> TYPE: DNA
<213> ORGANISM: Artificial Sequence
<220> FEATURE:
<223> OTHER INFORMATION: PCR primer

<400> SEQUENCE: 30
caggtgcagc tggtggagtc tgagggaggc ttggtccagc ctggggggtc cctgagactc      60
tcctgcgcag cctctagatt cacgtttagt aactattgga tgagctgggt ccgccaggct     120
ccagggaaag gctggagtg ggtggccaat ataaagcaag atggaagtga aaatattat       180
atggactctg tgaagggccg attcaccatc tccagagaca cgccaagaa ctcactgttt      240
ctgcagatga acaccctaag agccgaggac acggctatgt attactgtac gagggttagt    300
ttcggagtgc cgacgtatga cgattttttgg aggagttacg cgacgcccgc ttggtacttc   360
gattttggg gccgtggtac cctggtcact gtctcctca                             399

<210> SEQ ID NO 31
<211> LENGTH: 111
<212> TYPE: PRT
<213> ORGANISM: Homo sapiens

<400> SEQUENCE: 31

Gln Ser Ala Leu Ile Gln Pro Ala Ser Val Ser Gly Ser Pro Gly Gln
1               5                   10                  15

Ser Ile Thr Ile Ser Cys Thr Gly Ile Ser Ser Asp Asp Gly Tyr Tyr
            20                  25                  30

Lys Tyr Val Ser Trp Tyr Gln Gln Tyr Pro Gly Lys Ala Pro Lys Leu
        35                  40                  45

Met Ile Tyr Asp Val Ser Lys Arg Pro Ser Gly Ile Ser Phe Arg Phe
    50                  55                  60

```
Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Asn
                85                  90                  95

Met Thr Pro Tyr Val Phe Gly Thr Gly Thr Lys Val Thr Val Leu
            100                 105                 110

<210> SEQ ID NO 32
<211> LENGTH: 14
<212> TYPE: PRT
<213> ORGANISM: Homo sapiens

<400> SEQUENCE: 32

Thr Gly Ile Ser Ser Asp Asp Gly Tyr Tyr Lys Tyr Val Ser
1               5                   10

<210> SEQ ID NO 33
<211> LENGTH: 7
<212> TYPE: PRT
<213> ORGANISM: Homo sapiens

<400> SEQUENCE: 33

Asp Val Ser Lys Arg Pro Ser
1               5

<210> SEQ ID NO 34
<211> LENGTH: 11
<212> TYPE: PRT
<213> ORGANISM: Homo sapiens

<400> SEQUENCE: 34

Ser Ser Tyr Thr Ser Asn Met Thr Pro Tyr Val
1               5                   10

<210> SEQ ID NO 35
<211> LENGTH: 22
<212> TYPE: PRT
<213> ORGANISM: Homo sapiens

<400> SEQUENCE: 35

Gln Ser Ala Leu Ile Gln Pro Ala Ser Val Ser Gly Ser Pro Gly Gln
1               5                   10                  15

Ser Ile Thr Ile Ser Cys
            20

<210> SEQ ID NO 36
<211> LENGTH: 15
<212> TYPE: PRT
<213> ORGANISM: Homo sapiens

<400> SEQUENCE: 36

Trp Tyr Gln Gln Tyr Pro Gly Lys Ala Pro Lys Leu Met Ile Tyr
1               5                   10                  15

<210> SEQ ID NO 37
<211> LENGTH: 32
<212> TYPE: PRT
<213> ORGANISM: Homo sapiens

<400> SEQUENCE: 37

Gly Ile Ser Phe Arg Phe Ser Gly Ser Lys Ser Gly Asn Thr Ala Ser
1               5                   10                  15
```

```
Leu Thr Ile Ser Gly Leu Gln Ala Glu Asp Glu Ala Asp Tyr Tyr Cys
            20                  25                  30
```

<210> SEQ ID NO 38
<211> LENGTH: 10
<212> TYPE: PRT
<213> ORGANISM: Homo sapiens

<400> SEQUENCE: 38

```
Phe Gly Thr Gly Thr Lys Val Thr Val Leu
1               5                   10
```

<210> SEQ ID NO 39
<211> LENGTH: 333
<212> TYPE: DNA
<213> ORGANISM: Artificial Sequence
<220> FEATURE:
<223> OTHER INFORMATION: PCR primer

<400> SEQUENCE: 39

```
cagtctgctc tgattcagcc tgcctccgtg tctgggtctc ctggacagtc gatcaccatc      60
tcctgcactg gaattagtag tgacgatggt tattataagt atgtctcctg gtaccaacaa     120
tatccaggca aagcccccaa actcatgatt tatgatgtca gtaagcggcc ctcaggaatt     180
tcttttcgct tctctggctc caagtctggc aacacggcct ccctgaccat ctctgggctc     240
caggctgagg acgaggctga ttattactgc agctcatata caagtaacat gaccccctat     300
gtcttcggca ctgggaccaa ggtcaccgtc cta                                  333
```

<210> SEQ ID NO 40
<211> LENGTH: 119
<212> TYPE: PRT
<213> ORGANISM: Homo sapiens

<400> SEQUENCE: 40

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Val Ser Trp Asp Trp Ile Arg Gln Ser Pro Ser Arg Gly Leu Glu
        35                  40                  45

Trp Leu Gly Arg Thr Tyr Tyr Arg Ser Lys Trp Tyr Asn Glu Tyr Ala
50                  55                  60

Val Ser Val Glu Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Ile
                85                  90                  95

Tyr Phe Cys Val Arg Asn Asn Tyr Phe Phe Asp Leu Trp Gly Arg Gly
            100                 105                 110

Thr Leu Val Thr Val Ser Ser
        115
```

<210> SEQ ID NO 41
<211> LENGTH: 7
<212> TYPE: PRT
<213> ORGANISM: Homo sapiens

<400> SEQUENCE: 41

```
Ser Asn Ser Val Ser Trp Asp
1               5
```

<210> SEQ ID NO 42
<211> LENGTH: 18
<212> TYPE: PRT
<213> ORGANISM: Homo sapiens

<400> SEQUENCE: 42

Arg Thr Tyr Tyr Arg Ser Lys Trp Tyr Asn Glu Tyr Ala Val Ser Val
1               5                   10                  15

Glu Ser

<210> SEQ ID NO 43
<211> LENGTH: 7
<212> TYPE: PRT
<213> ORGANISM: Homo sapiens

<400> SEQUENCE: 43

Asn Asn Tyr Phe Phe Asp Leu
1               5

<210> SEQ ID NO 44
<211> LENGTH: 30
<212> TYPE: PRT
<213> ORGANISM: Homo sapiens

<400> SEQUENCE: 44

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser
            20                  25                  30

<210> SEQ ID NO 45
<211> LENGTH: 14
<212> TYPE: PRT
<213> ORGANISM: Homo sapiens

<400> SEQUENCE: 45

Trp Ile Arg Gln Ser Pro Ser Arg Gly Leu Glu Trp Leu Gly
1               5                   10

<210> SEQ ID NO 46
<211> LENGTH: 32
<212> TYPE: PRT
<213> ORGANISM: Homo sapiens

<400> SEQUENCE: 46

Arg Ile Thr Ile Asn Pro Asp Thr Ser Lys Asn Gln Phe Ser Leu Gln
1               5                   10                  15

Leu Asn Ser Val Thr Pro Glu Asp Thr Ala Ile Tyr Phe Cys Val Arg
            20                  25                  30

<210> SEQ ID NO 47
<211> LENGTH: 11
<212> TYPE: PRT
<213> ORGANISM: Homo sapiens

<400> SEQUENCE: 47

Trp Gly Arg Gly Thr Leu Val Thr Val Ser Ser
1               5                   10

<210> SEQ ID NO 48
<211> LENGTH: 357
<212> TYPE: DNA
<213> ORGANISM: Artificial Sequence

```
<220> FEATURE:
<223> OTHER INFORMATION: PCR primer

<400> SEQUENCE: 48
caggtacagc tgcagcagtc aggtccagga ctggtgaagc cctcgcagac cctctcactc    60
acctgtgcca tctccgggga cagtgtctct agcaacagtg tctcttggga ctggatcagg   120 cagtcccct cgaggggcct tgagtggctg ggaaggacat actataggtc caagtggtat    180
aatgagtatg cagtatctgt ggaaagtcga ataaccatca acccagacac atccaagaac   240
cagttctccc tgcaactgaa ctctgtgact cccgaggaca cggctatata tttctgtgta   300
agaaataact acttcttcga tctctggggc cgtggtaccc tggtcaccgt ctcctca      357

<210> SEQ ID NO 49
<211> LENGTH: 109
<212> TYPE: PRT
<213> ORGANISM: Homo sapiens

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asp Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Leu Arg Ser Asn Trp Pro Pro
                85                  90                  95

Gly Tyr Thr Phe Gly Gln Gly Thr Lys Val Glu Ile Lys
            100                 105

<210> SEQ ID NO 50
<211> LENGTH: 11
<212> TYPE: PRT
<213> ORGANISM: Homo sapiens

<400> SEQUENCE: 50

Arg Ala Ser Gln Ser Val Ser Ser Tyr Leu Ala
1               5                   10

<210> SEQ ID NO 51
<211> LENGTH: 7
<212> TYPE: PRT
<213> ORGANISM: Homo sapiens

<400> SEQUENCE: 51

Asp Ala Ser Asp Arg Ala Thr
1               5

<210> SEQ ID NO 52
<211> LENGTH: 11
<212> TYPE: PRT
<213> ORGANISM: Homo sapiens

<400> SEQUENCE: 52

Gln Leu Arg Ser Asn Trp Pro Pro Gly Tyr Thr
1               5                   10
```

```
<210> SEQ ID NO 53
<211> LENGTH: 23
<212> TYPE: PRT
<213> ORGANISM: Homo sapiens

<400> SEQUENCE: 53

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 54
<211> LENGTH: 15
<212> TYPE: PRT
<213> ORGANISM: Homo sapiens

<400> SEQUENCE: 54

Trp Tyr Gln Gln Lys Pro Gly Gln Ala Pro Arg Leu Leu Ile Tyr
1               5                   10                  15

<210> SEQ ID NO 55
<211> LENGTH: 32
<212> TYPE: PRT
<213> ORGANISM: Homo sapiens

<400> SEQUENCE: 55

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 56
<211> LENGTH: 10
<212> TYPE: PRT
<213> ORGANISM: Homo sapiens

<400> SEQUENCE: 56

Phe Gly Gln Gly Thr Lys Val Glu Ile Lys
1               5                   10

<210> SEQ ID NO 57
<211> LENGTH: 327
<212> TYPE: DNA
<213> ORGANISM: Artificial Sequence
<220> FEATURE:
<223> OTHER INFORMATION: PCR primer

<400> SEQUENCE: 57
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccgaca gggccactgg catcccagcc     180
aggttcagtg gcagtgggtc tgggacagac ttcactctca ccatcagcag ccttgagcct     240
gaagattttg cagtttatta ctgtcagctg cgtagcaact ggcctccggg gtacactttt     300
ggccagggga ccaaggtgga gatcaaa                                         327

<210> SEQ ID NO 58
<211> LENGTH: 24
<212> TYPE: DNA
<213> ORGANISM: Artificial Sequence
<220> FEATURE:
<223> OTHER INFORMATION: PCR primer
```

<400> SEQUENCE: 58
tctggtggtg gtggttctgc tagc                                          24

<210> SEQ ID NO 59
<211> LENGTH: 59
<212> TYPE: DNA
<213> ORGANISM: Artificial Sequence
<220> FEATURE:
<223> OTHER INFORMATION: PCR primer

<400> SEQUENCE: 59
gccagatctc gagctattac aagtcttctt cagaaataag cttttgttct agaattccg    59

<210> SEQ ID NO 60
<211> LENGTH: 20
<212> TYPE: DNA
<213> ORGANISM: Artificial Sequence
<220> FEATURE:
<223> OTHER INFORMATION: PCR primer

<400> SEQUENCE: 60
taatacgact cactataggg                                               20

<210> SEQ ID NO 61
<211> LENGTH: 24
<212> TYPE: DNA
<213> ORGANISM: Artificial Sequence
<220> FEATURE:
<223> OTHER INFORMATION: PCR primer

<400> SEQUENCE: 61
ggcagcccca taaacacaca gtat                                          24

<210> SEQ ID NO 62
<211> LENGTH: 119
<212> TYPE: PRT
<213> ORGANISM: Homo sapiens

<400> SEQUENCE: 62

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Asn Val Ser Ser Asn
            20                  25                  30

Gly Val Ser Trp Asp Trp Ile Arg Gln Ser Pro Ser Arg Gly Leu Glu
        35                  40                  45

Trp Leu Gly Arg Thr Tyr Tyr Arg Ser Lys Trp Tyr Asn Glu Tyr Ala
    50                  55                  60

Val Ser Val Glu Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Ile
                85                  90                  95

Tyr Phe Cys Val Arg Asn Asn Tyr Phe Phe Asp Leu Trp Gly Arg Gly
            100                 105                 110

Thr Leu Val Thr Val Ser Ser
        115

<210> SEQ ID NO 63
<211> LENGTH: 7
<212> TYPE: PRT
<213> ORGANISM: Homo sapiens

<400> SEQUENCE: 63

Ser Asn Gly Val Ser Trp Asp
1               5

<210> SEQ ID NO 64
<211> LENGTH: 30
<212> TYPE: PRT
<213> ORGANISM: Homo sapiens

<400> SEQUENCE: 64

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Asn Val Ser
            20                  25                  30

<210> SEQ ID NO 65
<211> LENGTH: 357
<212> TYPE: DNA
<213> ORGANISM: Artificial Sequence
<220> FEATURE:
<223> OTHER INFORMATION: PCR primer

<400> SEQUENCE: 65
caggtacagc tgcagcagtc aggtccagga ctggtgaagc cctcgcagac cctctcactc      60
acctgtgcca tctccgggga caatgtctct agcaacggtg tctcttggga ctggatcagg     120
cagtcccccT cgaggggcct tgagtggctg ggaaggacat actataggtc caagtggtat     180
aatgagtatg cagtatctgt ggaaagtcga ataaccatca acccagacac atccaagaac     240
cagttctccc tgcaactgaa ctctgtgact cccgaggaca cggctatata tttctgtgta     300
agaaataact acttcttcga tctctggggc cgtggtaccc tggtcaccgt ctcctca        357

<210> SEQ ID NO 66
<211> LENGTH: 119
<212> TYPE: PRT
<213> ORGANISM: Homo sapiens

<400> SEQUENCE: 66

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Val Ser Trp Asp Trp Ile Arg Gln Ser Pro Ser Arg Gly Leu Glu
        35                  40                  45

Trp Leu Gly Arg Thr Tyr Tyr Arg Ser Lys Trp Tyr Asn Glu Tyr Ala
    50                  55                  60

Val Ser Val Glu Asn Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Ile
                85                  90                  95

Tyr Phe Cys Val Arg Asn Asn Tyr Phe Phe Asp Leu Trp Gly Arg Gly
            100                 105                 110

Thr Leu Val Thr Val Ser Ser
        115

<210> SEQ ID NO 67
<211> LENGTH: 18
<212> TYPE: PRT
<213> ORGANISM: Homo sapiens

<400> SEQUENCE: 67

Arg Thr Tyr Tyr Arg Ser Lys Trp Tyr Asn Glu Tyr Ala Val Ser Val
1               5                   10                  15

Glu Asn

<210> SEQ ID NO 68
<211> LENGTH: 357
<212> TYPE: DNA
<213> ORGANISM: Artificial Sequence
<220> FEATURE:
<223> OTHER INFORMATION: PCR primer

<400> SEQUENCE: 68
caggtacagc tgcagcagtc aggtccagga ctggtgaagc cctcgcagac cctctcactc    60
acctgtgcca tctccgggga cagtgtctct agcaacagtg tctcttggga ctggatcagg   120
cagtccccct cgagggggcct tgagtggctg ggaaggacat actataggtc caagtggtat   180
aatgagtatg cagtatctgt ggaaaatcga ataaccatca cccagacac atccaagaac    240
cagttctccc tgcaactgaa ctctgtgact cccgaggaca cggctatata tttctgtgta   300
agaaataact acttcttcga tctctggggc cgtggtaccc tggtcaccgt ctcctca     357

<210> SEQ ID NO 69
<211> LENGTH: 119
<212> TYPE: PRT
<213> ORGANISM: Homo sapiens

<400> SEQUENCE: 69

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Val Ser Trp Asp Trp Ile Arg Gln Ser Pro Ser Arg Gly Leu Glu
        35                  40                  45

Trp Leu Gly Arg Thr Tyr Tyr Arg Ser Lys Trp Tyr Asn Glu Tyr Ala
    50                  55                  60

Val Ser Val Glu Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Ile
                85                  90                  95

Tyr Phe Cys Val Arg Asn Asp Tyr Phe Phe Asp Leu Trp Gly Arg Gly
            100                 105                 110

Thr Leu Val Thr Val Ser Ser
        115

<210> SEQ ID NO 70
<211> LENGTH: 7
<212> TYPE: PRT
<213> ORGANISM: Homo sapiens

<400> SEQUENCE: 70

Asn Asp Tyr Phe Phe Asp Leu
1               5

<210> SEQ ID NO 71
<211> LENGTH: 357
<212> TYPE: DNA
<213> ORGANISM: Artificial Sequence
<220> FEATURE:
<223> OTHER INFORMATION: PCR primer

<400> SEQUENCE: 71

```
caggtacagc tgcagcagtc aggtccagga ctggtgaagc cctcgcagac cctctcactc      60
acctgtgcca tctccgggga cagtgtctct agcaacagtg tctcttggga ctggatcagg     120
cagtcccct cgaggggcct tgagtggctg ggaaggacat actataggtc caagtggtat     180
aatgagtatg cagtatctgt ggaaagtcga ataaccatca acccagacac atccaagaac     240
cagttctccc tgcaactgaa ctctgtgact cccgaggaca cggctatata tttctgtgta     300
agaaatgact acttcttcga tctctggggc cgtggtaccc tggtcaccgt ctcctca       357
```

<210> SEQ ID NO 72
<211> LENGTH: 119
<212> TYPE: PRT
<213> ORGANISM: Homo sapiens

<400> SEQUENCE: 72

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Gly Val Ser Trp Asp Trp Ile Arg Gln Ser Pro Ser Arg Gly Leu Glu
        35                  40                  45

Trp Leu Gly Arg Thr Tyr Tyr Arg Ser Lys Trp Tyr Asn Glu Tyr Ala
    50                  55                  60

Val Ser Val Glu Asn Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Ile
                85                  90                  95

Tyr Phe Cys Val Arg Asn Asp Tyr Phe Phe Asp Leu Trp Gly Arg Gly
            100                 105                 110

Thr Leu Val Thr Val Ser Ser
        115
```

<210> SEQ ID NO 73
<211> LENGTH: 357
<212> TYPE: DNA
<213> ORGANISM: Artificial Sequence
<220> FEATURE:
<223> OTHER INFORMATION: PCR primer

<400> SEQUENCE: 73

```
caggtacagc tgcagcagtc aggtccagga ctggtgaagc cctcgcagac cctctcactc      60
acctgtgcca tctccgggga cagtgtctct agcaacggtg tctcttggga ctggatcagg     120
cagtcccct cgaggggcct tgagtggctg ggaaggacat actataggtc caagtggtat     180
aatgagtatg cagtatctgt ggaaaatcga ataaccatca acccagacac atccaagaac     240
cagttctccc tgcaactgaa ctctgtgact cccgaggaca cggctatata tttctgtgta     300
agaaatgact acttcttcga tctctggggc cgtggtaccc tggtcaccgt ctcctca       357
```

<210> SEQ ID NO 74
<211> LENGTH: 109
<212> TYPE: PRT
<213> ORGANISM: Homo sapiens

<400> SEQUENCE: 74

```
Glu Ile Val Leu Thr Gln Ser Pro Ala Thr Leu Ser Leu Ser Pro Gly
1               5                   10                  15
```

Glu Arg Ala Thr Leu Ser Cys Arg Ala Ser Gln Ser Val Gly Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Gly Tyr Thr Phe Gly Gln Gly Thr Lys Val Glu Ile Lys
            100                 105

<210> SEQ ID NO 75
<211> LENGTH: 11
<212> TYPE: PRT
<213> ORGANISM: Homo sapiens

<400> SEQUENCE: 75

Arg Ala Ser Gln Ser Val Gly Ser Tyr Leu Ala
1               5                   10

<210> SEQ ID NO 76
<211> LENGTH: 7
<212> TYPE: PRT
<213> ORGANISM: Homo sapiens

<400> SEQUENCE: 76

Asp Ala Ser Asn Arg Ala Thr
1               5

<210> SEQ ID NO 77
<211> LENGTH: 11
<212> TYPE: PRT
<213> ORGANISM: Homo sapiens

<400> SEQUENCE: 77

Gln Gln Arg Ser Asn Trp Pro Pro Gly Tyr Thr
1               5                   10

<210> SEQ ID NO 78
<211> LENGTH: 327
<212> TYPE: DNA
<213> ORGANISM: Artificial Sequence
<220> FEATURE:
<223> OTHER INFORMATION: PCR primer

<400> SEQUENCE: 78
gaaattgtgt tgacacagtc tccagccacc ctgtctttgt ctccagggga aagagccacc      60
ctctcctgca gggccagtca gagtgttggc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag ccttgagcct     240
gaagattttg cagtttatta ctgtcagcag cgtagcaact ggcctccggg gtacactttt     300
ggccagggga ccaaggtgga gatcaaa                                         327

<210> SEQ ID NO 79
<211> LENGTH: 119
<212> TYPE: PRT
<213> ORGANISM: Homo sapiens -continued

```
<400> SEQUENCE: 79

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Val Ser Trp Asp Trp Ile Arg Gln Ser Pro Ser Arg Gly Leu Glu
        35                  40                  45

Trp Leu Gly Arg Thr Tyr Tyr Arg Ser Lys Trp Tyr Asn Glu Tyr Ala
    50                  55                  60

Val Ser Val Glu Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Ile
            85                  90                  95

Tyr Phe Cys Val Arg Asn Asp Tyr Phe Phe Asp Leu Trp Gly Arg Gly
            100                 105                 110

Thr Leu Val Thr Val Ser Ser
            115

<210> SEQ ID NO 80
<211> LENGTH: 357
<212> TYPE: DNA
<213> ORGANISM: Artificial Sequence
<220> FEATURE:
<223> OTHER INFORMATION: PCR primer

<400> SEQUENCE: 80
caggtacagc tgcagcagtc aggtccagga ctggtgaagc cctcgcagac cctctcactc      60
acctgtgcca tctccgggga cagtgtctct agcaacagtg tctcttggga ctggatcagg     120 cagtcccect cgagggggcct tgagtggctg ggaaggacat actataggtc caagtggtat     180
aatgagtatg cagtatctgt ggaaagtcga ataaccatca cccagacac atccaagaac     240 cagttctccc tgcaactgaa ctctgtgact cccgaggaca cggctatata tttctgtgta     300
agaaatgact acttcttcga tctctggggc cgtggtaccc tggtcaccgt ctcctca       357
```

ANTI-OX40 ANTIBODY AND APPLICATION THEREOF

CROSS-REFERENCE TO RELATED APPLICATIONS

This application claims priority under 35 U.S.C. § 371 to Patent Cooperation Treaty application PCT/CN2015/091958, filed Oct. 15, 2015, the entire contents of which are incorporated herein by reference.

SEQUENCE LISTING

This application incorporates in its entirety the Sequence Listing entitled "262790-425456_Sequence_Listing_ST25.txt" (31,839 bytes), which was created on Apr. 12, 2018 and filed electronically herewith.

FIELD OF THE INVENTION

The present invention relates to the field of medical biology, in particular to an anti-OX40 antibody and application thereof.

BACKGROUND OF THE INVENTION

T cell activation requires synergism between two signals: the first signal is generated by recognizing production of an antigen by a T cell antigen receptor (TCR) and is transduced into the cell via a CD3 molecule, the first signal determines the specificity of T cells in adaptive immune response; the second signal is generated by the interaction between co-stimulatory molecules on the surface of antigen-presenting cells (APCs) or target cells with corresponding co-stimulatory molecule receptors on the surface of T cells. Co-stimulatory signals stimulate antigen-specific T cells to proliferate and differentiate into effector T cells. In the absence of co-stimulatory signals, T cells will enter the non-responsive or autoimmune-tolerance state and even enter into programmed death.

OX40, also known as TNFRSF4, ACT35, CD134, IMD16 or TXGP1L, is a member of the TNFR receptor superfamily and is a type I transmembrane glycoprotein. OX40 is mainly expressed on activated CD4+T cells and CD8+T cells (Paterson et al. (1987) Mol Immunol 24: 1281-1290). The extracellular segment of OX40 consists of three cysteine-rich domains and one C-terminal incomplete CRD (Deanne M et al. (2006) Structure 14: 1321-1330). OX40 is a secondary co-stimulatory molecule. Unlike CD28, OX40 is not expressed on the surfaces of resting T-cells but is highly expressed 24-72 hours after T-cell activation. The ligand OX40L (TNFSF4, TXGP1, OX-40L, gp34 or CD252) of OX40 is a type II transmembrane glycoprotein and is expressed on activated antigen presenting cells such as dendritic cells, B cells, etc. (Godfrey, W R et al. (1994) J Exp Med 180: 757-762). The OX40/OX40L signal plays a very important role in the activation, proliferation and apoptosis inhibition of T cells. Studies show that activated OX40 antibodies can effectively promote the proliferation and activation of T cells and produce better anti-tumor effects (Brendan D. Curti et al. (2013) Cancer Res 73: 7189-7198).

The use of OX40-activating antibodies in combination with other methods of treating tumors is reviewed and described in detail by Stefanie N. Linch et al. (Stefanie N. Linch et al. (2015) frontiers in oncology 5: 1-14). It has also been reported that the survival of mice can be significantly prolonged when OX40-activating antibodies are used in combination with radiotherapy (Gough M J et al. (2010) J Immunother 33 (8): 798-809; Kjaergaard J et al. (2005) 103 (1): 156-164).

There remains a need in the art for anti-OX40 antibodies that are capable of binding with high affinity to OX40 and have OX40 agonist activity.

SUMMARY OF THE INVENTION

In order to solve the above technical problem, the object of the present invention is to provide an anti-OX40 antibody with good specificity, high affinity and stability and application thereof.

The first aspect of the present invention relates to an anti-OX40 antibody or an antigen-binding site thereof, containing a set of CDRs selected from the following:

1) VH CDR1, CDR2 and CDR3 having sequences as shown by SEQ ID NO: 5-7 respectively and VL CDR1, CDR2 and CDR3 having sequences as shown by SEQ ID NO: 14-16 respectively, or heavy chain variable regions and light chain variable regions having sequences: a) binding to the same epitope as and/or b) being 70%, 80%, 85%, 90% or 97% identical to SEQ ID NO: 5-7 and SEQ ID NO: 14-16 respectively;

2) VH CDR1, CDR2 and CDR3 having a sequence as shown by SEQ ID NO: 23-25 respectively and VL CDR1, CDR2 and CDR3 having sequences as shown by SEQ ID NO: 32-34 respectively, or heavy chain variable regions and light chain variable regions having sequences: a) binding to the same epitope as and/or b) being 70%, 80%, 85%, 90% or 97% identical to SEQ ID NO: 23-25 and SEQ ID NO: 32-34 respectively;

3) VH CDR1, CDR2 and CDR3 having sequences as shown by SEQ ID NO: 41-43 respectively and VL CDR1, CDR2 and CDR3 having sequences as shown by SEQ ID NO: 50-52 respectively, or heavy chain variable regions and light chain variable regions having sequences: a) binding to the same epitope as and/or b) being 70%, 80%, 85%, 90% or 97% identical to SEQ ID NO: 41-43 and SEQ ID NO: 50-52 respectively.

The anti-OX40 antibody or the antigen-binding site thereof according to any one set forth in the first aspect of the present invention further contains a set of VH framework regions, selected from the following:

1) VH FR1, FR2, FR3 and FR4 having sequences as shown by SEQ ID NO: 8-11 respectively;
2) VH FR1, FR2, FR3 and FR4 having sequences as shown by SEQ ID NO: 26-29 respectively;
3) VH FR1, FR2, FR3 and FR4 having sequences as shown by SEQ ID NO: 44-47 respectively.

The anti-OX40 antibody or the antigen-binding site thereof according to any one set forth in the first aspect of the present invention further contains a set of VL framework regions, selected from the following:

1) VL FR1, FR2, FR3 and FR4 having sequences as shown by SEQ ID NO: 17-20 respectively;
2) VL FR1, FR2, FR3 and FR4 having sequences as shown by SEQ ID NO: 35-38 respectively;
3) VL FR1, FR2, FR3 and FR4 having sequences as shown by SEQ ID NO: 53-56 respectively.

The anti-OX40 antibody or the antigen-binding portion thereof according to any set forth in the first aspect of the present invention contains heavy chain variable regions each having a sequence of SEQ ID NO: 4, 22 and 40 or a sequence: a) binding to the same epitope as and/or b) being 70%, 80%, 85%, 90% or 97% identical to SEQ ID NO: 4, 22 and 40;

further contains heavy chain variable regions each having a sequence of SEQ ID NO: 4, 22 and 40 or contains VH CDRs having sequences: a) binding to the same epitope and/or b) having no more than 3 mutated amino acids, as compared to SEQ ID NO: 4, 22 and 40;

further contains heavy chain variable regions each having a sequence of SEQ ID NO: 4, 22, 40, 62, 66, 69, 72 and 79.

The anti-OX40 antibody or the antigen-binding site thereof according to any set forth in the first aspect of the present invention contains light chain variable regions each having a sequence of SEQ ID NO: 13, 31 and 49 or contains VL CDRs having sequences: a) binding to the same epitope as and/or b) being 70%, 80%, 85%, 90% or 97% identical to SEQ ID NO: 13, 31 and 49;

further contains light chain variable regions each having a sequence of SEQ ID NO: 13, 31 and 49 or a sequence a) binding to the same epitope and/or b) having no more than 3 mutated amino acids, as compared to SEQ ID NO: 13, 31 and 49;

further contains light chain variable regions each having a sequence of SEQ ID NO: 13, 31, 49 and 74.

The anti-OX40 antibody or the antigen-binding site thereof according to any set forth in the first aspect of the present invention is a complete antibody, a bispecific antibody, scFv, Fab, Fab', F(ab')2 or Fv.

In one embodiment of the present invention, when the anti-OX40 antibody or the antigen-binding site thereof is scFv, linker peptides may be contained between the heavy chain variable regions and the light chain variable regions, and the sequence of the linker peptides is as shown by SEQ ID NO: 1.

The anti-OX40 antibody or the antigen-binding site thereof according to any set forth in the first aspect of the present invention contains heavy chain constant regions selected from IgG, IgM, IgE, IgD and IgA.

In an embodiment of the present invention, the heavy chain constant regions are selected from IgG1, IgG2, IgG3 and IgG4.

In an embodiment of the present invention, the heavy chain constant regions are IgG1 or IgG4.

The anti-OX40 antibody or the antigen-binding site thereof according to any one set forth in the first aspect of the present invention contains κ or λ light chain constant regions.

The second aspect of the present invention relates to a nucleic acid molecule, containing a nucleic acid sequence capable of encoding heavy chain variable regions of an antibody, and each heavy chain variable region contains an amino acid sequence selected from the following:
(1) SEQ ID NO: 5-7;
(2) SEQ ID NO: 23-25;
(3) SEQ ID NO: 41-43;
(4) a sequence a) binding to the same epitope as and/or b) being 70%, 80%, 85%, 90% or 97% identical to (1)-(3).

Further, each heavy chain variable region contains an amino acid sequence selected from the following:
SEQ ID NO: 4, 22 and 40, or a sequence a) binding to the same epitope as and/or b) being 70%, 80%, 85%, 90% or 97% identical to SEQ ID NO: 4, 22 and 40.

Furthermore, heavy chain variable regions each having a sequence of SEQ ID NO: 4, 22 and 40 or a sequence a) binding to the same epitope and/or b) having no more than 3 mutated amino acids, as compared to SEQ ID NO: 4, 22 and 40, are contained.

Furthermore, heavy chain variable regions each having a sequence of SEQ ID NO: 4, 22, 40, 62, 66, 69, 72 and 79 are contained.

In an embodiment of the present invention, the nucleic acid molecule further contains a nucleic acid sequence capable of encoding heavy chain constant regions of an antibody, and the heavy chain constant regions are selected from IgG, IgM, IgE, IgD and IgA.

In an embodiment of the present invention, the heavy chain constant regions are selected from IgG1, IgG2, IgG3 and IgG4.

In an embodiment of the present invention, the heavy chain constant regions are IgG1 or IgG4.

The third aspect of the present invention relates to a nucleic acid molecule, containing a nucleic acid sequence capable of encoding light chain variable regions of an antibody, and each light chain variable region contains an amino acid sequence selected from the following:
(1) SEQ ID NO: 14-16;
(2) SEQ ID NO: 32-34;
(3) SEQ ID NO: 50-52;
(4) a sequence a) binding to the same epitope as and/or b) being 70%, 80%, 85%, 90% or 97% identical to (1)-(3).

Furthermore, each of the light chain variable regions contains an amino acid sequence selected from the following:
SEQ ID NO: 13, 31 and 49, or a sequence: a) binding to the same epitope as and/or b) being 70%, 80%, 85%, 90% or 97% identical to SEQ ID NO: 13, 31 and 49.

Furthermore, the light chain variable region each having a sequence of SEQ ID NO: 13, 31 and 49 or a sequence a) binding to the same epitope and/or b) having no more than 3 mutated amino acids, as compared to SEQ ID NO: 13, 31 and 49, are contained.

Furthermore, the light chain variable regions each having a sequence of SEQ ID NO: 13, 31, 49 and 74, are contained.

In an embodiment of the present invention, the nucleic acid molecule further contains a nucleic acid sequence capable of encoding light chain constant regions of an antibody, and the light chain constant regions are κ or λ light chain constant regions.

The fourth aspect of the present invention relates to a vector containing the nucleic acid molecule according to any set forth in the second or third aspect of the present invention.

The vector according to any set forth in the fourth aspect of the present invention contains the nucleic acid molecule according to any set forth in the second aspect of the present invention and the nucleic acid molecule according to any set forth in the third aspect.

The fifth aspect of the present invention relates to a host cell, containing the nucleic acid molecule according to any one set forth in the second or third aspect of the present invention or the vector according to any one set forth in the fourth aspect of the present invention.

The sixth aspect of the present invention relates to a conjugate, containing the anti-OX40 antibody or the antigen-binding site thereof according to any set forth in the first aspect of the present invention, and other biologically active substances, the anti-OX40 antibody or antigen-binding site thereof is conjugated, either directly or through a linker, to the other biologically active substances.

In an embodiment of the present invention, the other biologically active substances are selected from chemical substances, polypeptides, enzymes, cytokines or other biologically active single substances or mixed substances, such as interleukins, tumor necrosis factors, chemokines, nanoparticles and the like, which can indirectly inhibit the growth of tumor cells or inhibit or kill tumor cells by activating the body's immune response so as to treat tumors.

The seventh aspect of the present invention relates to a composition (e.g., a pharmaceutical composition), containing the anti-OX40 antibody or the antigen-binding site thereof according to any set forth in the first aspect of the present invention, the nucleic acid molecule according to any set forth in the second aspect or the third aspect, the vector according to any set forth in the fourth aspect, the host cell according to any set forth in the fifth aspect, or the conjugate according to any set forth in the sixth aspect of the present invention, and optionally a pharmaceutically acceptable carrier or excipient, and optionally other biologically active substances. The composition according to any set forth in the seventh aspect of the present invention (e.g., a pharmaceutical composition), the other biologically active substances include but are not limited to other antibodies, fusion proteins or drugs (e.g., anti-tumor drugs such as radiotherapy or chemotherapy drugs).

The present invention also relates to the use of the anti-OX40 antibody or the antigen-binding site thereof according to any set forth in the first aspect of the present invention, the nucleic acid molecule according to any set forth in the second aspect or the third aspect, the vector according to any set forth in the fourth aspect, the host cell according to any set forth in the fifth aspect, the conjugate according to any set forth in the sixth aspect, or the composition according to any set forth in the seventh aspect for the preparation of a medicament for the prevention or treatment of tumors.

With the above-described solutions, the present invention has at least the following advantages:

In the present invention, an anti-OX40 antibody is obtained by means of screening with a yeast display technology and further affinity maturation, the anti-OX40 antibody has good specificity, high affinity and stability, can specifically bind to human OX40, and can enhance the activation of T cells through binding to activated T cell and thus has a significant inhibitory effect on tumor growth. In addition, the anti-OX40 antibody of the present invention is a fully human antibody, which has a lower immunogenicity, less rejection in patients, and better drug-forming potential than the conventional murine, chimeric and humanized antibodies.

The above description is merely a summary of the technical solutions of the present invention. In order to understand the technical solutions of the present invention more clearly and implement the solutions according to the description, the preferred embodiments of the present invention will be described in detail below with reference to the accompanying drawings.

DETAILED DESCRIPTION OF THE EMBODIMENTS

Figure 1:
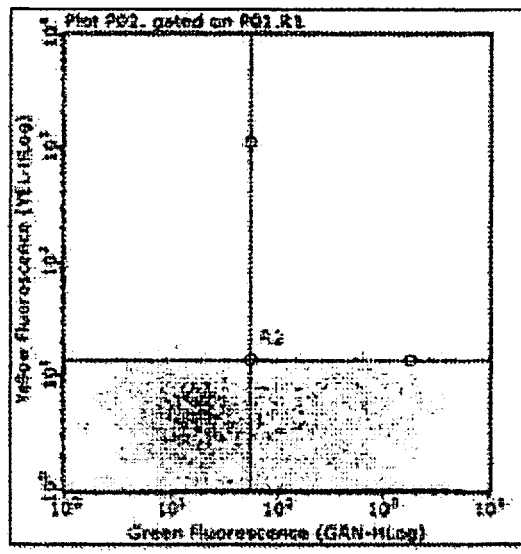
FIG. 1 is a graph showing the results of the binding of purified anti-hOX40 scFv to hOX40, where the x-axis indicates the fluorescence intensity of EGFP and the y-axis indicates the fluorescence intensity of anti-hIg-PE.
Figure 1:
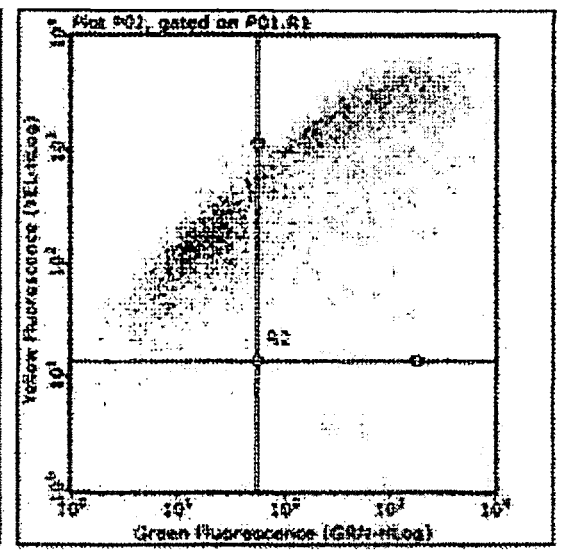
Figure 1:
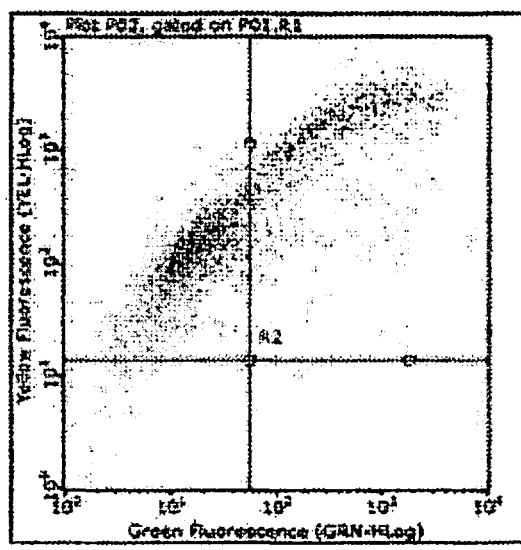
Figure 1:
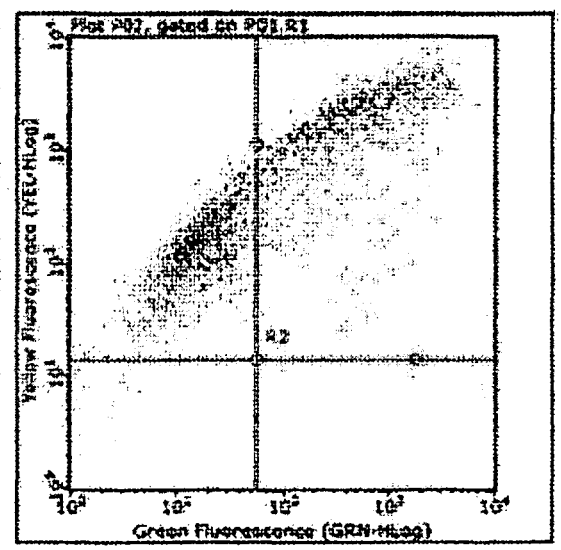

Specific embodiments of the present invention are described in further details below with reference to the figures and embodiments. The following embodiments illustrate the present invention but are not intended to limit the scope of the present invention.

The present invention is further described as below: in the present invention, unless otherwise specified, the scientific and technical terms used herein have the meanings commonly understood by those skilled in the art. Also, the protein and nucleic acid chemistry, molecular biology, cell and tissue culture, microbiology, immunology-related terms, and laboratory procedures used herein are terms and routine steps that are widely used in the relevant art. In the meantime, in order to better understand the present invention, definitions and explanations of related terms are provided below.

In the present invention, the term "antibody" refers to an immunoglobulin molecule usually composed of two identical pairs of polypeptide chains each having one "light" (L) chain and one "heavy" (H) chain. The light chains of an antibody can be classified as κ and λ light chains. The heavy chains can be classified as μ, δ, γ, α or ε, and the isotypes of an antibody are defined as IgM, IgD, IgG, IgA and IgE, respectively. Within the light and heavy chains, the variable and constant regions are joined by a "J" region of about 12 or more amino acids, and the heavy chains further comprise a "D" region of about 3 or more amino acids. Each heavy chain consists of a heavy chain variable region (VH) and a heavy chain constant region (CH). The heavy chain constant region consists of three domains (CH1, CH2 and CH3). Each light chain consists of a light chain variable region (VL) and a light chain constant region (CL). The light chain constant region consists of one domain, CL. The constant region of an antibody may mediate binding of the immunoglobulin to the host tissue or factor, including various cells of the immune system (e.g., effector cells) and the first component (C1q) of the classical complement system. The VH and VL regions can also be subdivided into regions with high variability known as complementarity determining regions (CDRs) interspersed with more conserved regions known as framework regions (FRs). Each VH and VL consists of 3 CDRs and 4 FRs arranged from N-terminal to C-terminal in the following order: FR1, CDR1, FR2, CDR2, FR3, CDR3, FR4. The variable regions (VH and VL) of each heavy/light chain pair form the antibody binding site, respectively. Distribution of amino acids to regions or domains follows the definition of Kabat Sequences of Proteins of Immunological Interest (National Institutes of Health, Bethesda, Md. (1987 and 1991)), or Chothia & Lesk (1987) J. Mol. Biol. 196:901-917; Chothia et al. (1989) Nature 342:878-883. The amino acid positions described in the present invention are based on an online comparison of abysis tools (http://www.bioinf.org.uk/abysis/index.html) and do not represent actual positions in the amino acid sequence.

The term "antibody" is not limited by any particular antibody-producing method. For example, it includes, in particular, recombinant antibodies, monoclonal antibodies and polyclonal antibodies. Antibodies may be antibodies of different isotypes, e.g., IgG (e.g., IgG1, IgG2, IgG3 or IgG4 subtype), IgA1, IgA2, IgD, IgE or IgM antibody.

In the present invention, the term "antigen-binding site" of an antibody refers to one or more sites of a full-length antibody that retains the ability to bind the same antigen to which the antibody binds (e.g., OX40) and competes against an intact antibody for an antigen specific binding. See generally, Fundamental Immunology, Ch. 7 (Paul, W., ed., 2nd, Raven Press, N.Y. (1989), which is incorporated herein by reference in its entirety for all purposes. Antigen-binding sites can be produced by recombinant DNA techniques or by enzymatic or chemical cleavage of intact antibodies. In some cases, the antigen binding site includes Fab, Fab ', F (ab') 2, Fd, Fv, dAb and complementarity determining region (CDR) fragments, single chain antibodies (e.g., scFv), chimeric antibodies, diabodies, and polypeptides that comprise at least a portion of an antibody that is sufficient to confer specific antigen-binding ability to the polypeptide.

In the present invention, the term "vector" refers to a nucleic acid vehicle into which a polynucleotide encoding a protein can be inserted and expressed. The genetic material elements carried in the vector can be expressed in a host cell by transforming, transducing, or transfecting the host cell with the vector. Embodiments of vectors include: plasmids; phagemids; cosmos; artificial chromosomes such as yeast artificial chromosomes (YACs), bacterial artificial chromosomes (BACs) or P1-derived artificial chromosomes (PACs); phages such as λ phage or M13 phage and animal viruses. Animal virus used as a carrier include retrovirus (including lentivirus), adenovirus, adeno-associated virus, herpes virus (such as herpes simplex virus), jaundice virus, baculovirus, papilloma virus, papovaviruses (such as SV40). A vector may contain a variety of elements that control expression, including promoter sequences, transcriptional initiation sequences, enhancer sequences, selection elements, and reporter genes. In addition, the vector may also contain an origin of replication. It is also possible that the vector may include components that assist its entry into the cell, such as viral particles, liposomes or protein shells, but not only these substances.

In the present invention, the term "host cell" refers to a cell into which a vector is introduced and includes many cell types such as prokaryotic cells such as *Escherichia coli* and *Bacillus subtilis*, fungal cells such as yeast cells or *Aspergillus* cells, insect cells such as S2 *Drosophila* cells or Sf9, or animal cells such as fibroblasts, CHO cells, COS cells, NSO cells, HeLa cells, BHK cells, HEK293 cells or human cells.

In the present invention, "specifically binding" refers to a non-random binding reaction between two molecules, for example, a reaction between an antibody and an antigen that produces the antibody. Here, the binding affinity of the antibody that binds the first antigen to the second antigen is undetectable or weak. In certain embodiments, an antigen-specific antibody refers to an antibody that binds to the antigen with an affinity (KD)≤$10^{-5}$ M (e.g. $10^{-6}$ M, $10^{-7}$ M, $10^{-8}$ M, $10^{-9}$ M, $10^{-10}$ M, etc.), where KD refers to the ratio of dissociation rate to binding rate ($k_{off}/k_{on}$), which can be determined using methods familiar to one skilled in the art.

Embodiment 1: Expression of Recombinant Human OX40 and Preparation of Related EGFP Cells S1.1 The amino acid sequence of the human OX40 (hOX40) extracellular domain (i.e., the residue 1 to the residue 216 in P43489) was obtained based on the amino acid sequence of human OX40 (P43489) in the Uniprot protein database;

S1.2 The amino acid sequence of the human IgG1-Fc (hFc) domain (i.e., the residue 104 to the residue 330 in P01857) was obtained based on the constant region amino acid sequence of human immunoglobulin gametal (IgG1) (P01857) in the Uniprot protein database;

S1.3 The amino acid sequence of the mouse IgG1-Fc (muFc) domain (i.e., the residue 98 to the residue 324 in P01868) was obtained based on the constant region amino acid sequence (P01868) of mouse immunoglobulin gametal (IgG1) in the Uniprot protein database;

S1.4 The DNA fragments encoding the amino acid sequences in steps S1.1 to S1.3 were obtained by artificial synthesis. The synthesized gene sequences were sub-cloned into the commercial vector pcDNA4/myc-HisA (Invitrogen, V863-20) by double digestion by HindIII and EcoRI (Fermentas), respectively, and the accuracy of the constructed plasmid was verified by sequencing to obtain recombinant the plasmid DNA i.e., pcDNA4-hOX40-hFc and pcDNA4-hOX40-muFc;

S1.5 The amino acid sequences of EGFP (C5MKY7), human OX40 (P43489), mouse OX40 (P47741), human CD137 (Q07011) and human CD27 (P26842) were obtained based on the information in Uniprot protein database;

S1.6 The DNA fragments encoding the amino acid sequences in steps S1.5 were obtained synthetically, the synthesized gene sequences were sub-cloned into the commercial vector pcDNA4/myc-HisA (Invitrogen, V863-20) by double digestion by HindIII and EcoRI (Fermentas), respectively, and the accuracy of the constructed plasmid was verified by sequencing to obtain the recombinant plasmid DNA i.e., pcDNA4-hOX40-EGFP, pcDNA4-hCD137-EGFP, pcDNA4-mOX40-EGFP and pcDNA4-hCD27-EGFP;

S1.7 The EGFP recombinant plasmid in step S1.6 was transfected into HEK293 (ATCC, CRL-1573™) cells, and the expression of hOX40, hCD137, mOX40 and hCD27 was confirmed by fluorescence activated signal sorting (FACS) 48 h after transfection.

S1.8 pcDNA4-hOX40-Fc and pcDNA4-hOX40-muFc were transiently transfected into HEK293 cells for protein production. The recombinant expression plasmids were diluted with FreeStyle293 medium and PEI (polyethylenimine) solution for transformation was added; each group of plasmid/PEI mixture was added to the cell suspension respectively and incubated at 37° C., 10% CO2 and 90 rpm; after 5-6 days, culture supernatant was collected and purified by Protein A affinity chromatography to obtain hOX40-Fc, hOX40-muFc protein samples for the following embodiments. The obtained protein samples were subjected to preliminary detection by SDS-PAGE, and the target band can be clearly seen.

Embodiment 2: Screening, Cloning, Expressing and Identification of Anti-hOX40 Antibody from Yeast Display Library 2.1 Methods Yeast display technology was used to screen for the whole human antibodies against human OX40. The scFV yeast display library was constructed by cloning the VH and VL genes in the IgM and IgG cDNA from PBMCs from 150 healthy human beings (The linker sequence between the VH and VL is GGGGSGGGGSGGGGS (SEQ ID NO: 1) linker peptide). The library volume is $5 \times 10^8$. The 10-fold volume of yeast library was resuscitated to induce the expression of the antibody on yeast surface; the yeasts were enriched twice with 100 nM antigens for biotinylated hOX40 using magnetic bead sorting, and then further enriched twice using FACS for biotinylated hOX40. The enriched yeasts were coated on the plate, and monoclones were picked from it. After amplification and induction of expression of the monoclonal yeasts, the monoclonal yeasts were analyzed by staining using anti-myc antibody and biotinylated hOX40 or control antigen hCD137. The yeasts with positive antigen/negative control yeasts were identified as positive yeasts.

The yeast clones confirmed by FACS were subjected to yeast colony PCR and sequencing. The PCR primers were: sequence-F: CGTAGAATCGAGACCGAGGAGA (SEQ ID NO: 2); sequence-R: CTGGTGGTGGTGGTTCTGCTAGC (SEQ ID NO: 3). Sequencing primers were sequence-R. After sequencing, BioEdit software was used for sequence alignment and analysis.

The gene of the single-chain antibody scFv obtained above was fused with the above human IgG1-Fc gene, and then double-digested with HindIII and EcoRI (Fermentas) and cloned into the commercial vector pcDNA4/myc-HisA. The cloning and extraction in small amount of the plasmid were carried out according to the standard operation of Molecular Cloning. The extracted plasmid was transiently expressed in HEK293 cells and purified by protein A column.

The hOX40-EGFP cells were resuspended in 0.5% PBS-BSA Buffer, and 2 μg of the above purified anti-hOX40 scFv antibody was added, and the relevant control was set at the same time. The negative control was 2 μg of hIgG1 protein. The secondary antibody is anti-hIg-PE (eBioscience). After staining, flow cytometry was performed. In this way, antibodies that bind to the hOX40 antigen on cell surface were identified.

After screening and identification, three better antibodies O3 scFv, O19scFv and O21scFv were obtained. As shown in FIG. 1, the three anti-hOX40 antibodies were able to bind to the hOX40 on cell surface whereas the negative control was unable to bind to the hOX40 on cell surface. A linker with a sequence of GGGGSGGGGSGGGGS (SEQ ID NO: 1) was between the heavy and light chain variable regions of the above antibodies.

2.2 Sequences 2.2.1 the Amino Acid Sequence of Each Heavy Chain Variable Region of O3 scFv is:

(SEQ ID NO: 4)
QVQLQQWGAGLLKPSETLSLTCGFNGEYFTDYFWTWVRQPPGEALEWLA

LIYWDDDERYSPSLKNRLIITKDISKNQVVLTMTHMEPADTGTYYCARW

GGSLMNAFDVWGPGTMVTVSS where the underlined parts are CDR1, CDR2 and CDR3, respectively, and the sequence numbers thereof are SEQ ID NOs: 5-7, respectively; the parts without underline are FR1, FR2, FR3 and FR4, respectively, with the sequence numbers of SEQ ID NOs: 8-11, respectively.

The DNA sequence corresponding to the amino acid sequence of each heavy chain variable region of O3 scFv is:

(SEQ ID NO: 12)
CAGGTGCAGCTACAGCAGTGGGGCGCAGGACTGTTGAAGCCTTCGGAGAC

CCTGTCCCTCACCTGCGGTTTCAATGGAGAATACTTCACTGATTACTTCT

GGACCTGGGTCCGGCAGCCCCCCGGAGAGGCCCTGGAGTGGCTTGCACTC

ATTTATTGGGATGATGATGAGCGCTACAGCCCATCTCTGAAGAACAGACT

CATCATCACCAAGGACATTTCCAAAAACCAGGTGGTCCTTACAATGACCC

ACATGGAGCCTGCGGACACAGGCACCTATTACTGTGCGAGATGGGGTGGT

TCTTTAATGAACGCTTTTGATGTCTGGGGCCCAGGGACAATGGTCACCGT

CTCTTCA

The amino acid sequence of each light chain variable region of O3 scFv is:

(SEQ ID NO: 13)
QSALIQPASVSGSPGQSITISCTGTSSDVGGYNYVSWYQRHPGKAPRLMI

YDVTKRPSGVSNRFSGSKSGNTASLTISGLQAEDEADYYCSSYTSSSIAV

FGGGTQLTVL where the underlined parts are CDR1, CDR2 and CDR3, respectively, with the sequence numbers of SEQ ID NOs: 14-16, respectively; the parts without underline are FR1, FR2, FR3 and FR4, respectively, with the sequence numbers of SEQ ID NOs:17-20, respectively.

the DNA sequence corresponding to the amino acid sequence of each light chain variable region of O3 scFv is:

(SEQ ID NO: 21)
CAGTCTGCCCTGATTCAGCCTGCCTCCGTGTCTGGGTCTCCTGGACAGTC

GATCACCATCTCCTGCACTGGAACCAGTAGTGACGTTGGTGGTTATAATT

ATGTCTCCTGGTACCAACGACACCCAGGCAAAGCCCCCAGACTCATGATT

TATGATGTCACTAAGCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATACAAGCAGCAGCATTGCTGTG

TTCGGAGGAGGCACCCAGCTGACCGTCCTC 2.2.2 the Amino Acid Sequence of Each Heavy Chain Variable Region of O19 scFv:

(SEQ ID NO: 22)
QVQLVESEGGLVQPGGSLRLSCAASRFTFSNYWMSWVRQAPGKGLEWVAN

IKQDGSEKYYMDSVKGRFTISRDNAKNSLFLQMNTLRAEDTAMYYCTRVS

FGVPTYDDFWRSYATPAWYFDFWGRGTLVTVSS where the underlined parts are CDR1, CDR2 and CDR3, respectively, with the sequence numbers of SEQ ID NOs: 23-25, respectively; the parts without underline are FR1, FR2, FR3 and FR4, respectively, with the sequence numbers of SEQ ID NOs:26-29, respectively.

The DNA sequence corresponding to the amino acid sequence of each heavy chain variable region of O19 scFv is:

(SEQ ID NO: 30)
CAGGTGCAGCTGGTGGAGTCTGAGGGAGGCTTGGTCCAGCCTGGGGGGTC

CCTGAGACTCTCCTGCGCAGCCTCTAGATTCACGTTTAGTAACTATTGGA

TGAGCTGGGTCCGCCAGGCTCCAGGGAAAGGGCTGGAGTGGGTGGCCAAT

ATAAAGCAAGATGGAAGTGAGAAATATTATATGGACTCTGTGAAGGGCCG

ATTCACCATCTCCAGAGACAACGCCAAGAACTCACTGTTTCTGCAGATGA

ACACCCTAAGAGCCGAGGACACGGCTATGTATTACTGTACGAGGGTTAGT

TTCGGAGTGCCGACGTATGACGATTTTTGGAGGAGTTACGCGACGCCCGC

TTGGTACTTCGATTTTTGGGGCCGTGGTACCCTGGTCACTGTCTCCTCA

The amino acid sequence of each light chain variable region of O19 scFv is:

(SEQ ID NO: 31)
QSALIQPASVSGSPGQSITISCTGISSDDGYYKYVSWYQQYPGKAPKLMI

YDVSKRPSGISFRFSGSKSGNTASLTISGLQAEDEADYYCSSYTSNMTPY

VFGTGTKVTVL where the underlined parts are CDR1, CDR2 and CDR3, respectively, with the sequence numbers of SEQ ID NOs: 32-34, respectively; the parts without underline are FR1, FR2, FR3 and FR4, respectively, with the sequence numbers of SEQ ID NOs:35-38, respectively.

The DNA sequence corresponding to the amino acid sequence of each light chain variable region of O19 scFv is:

(SEQ ID NO: 39)
CAGTCTGCTCTGATTCAGCCTGCCTCCGTGTCTGGGTCTCCTGGACAGTC

GATCACCATCTCCTGCACTGGAATTAGTAGTGACGATGGTTATTATAAGT

ATGTCTCCTGGTACCAACAATATCCAGGCAAAGCCCCCAAACTCATGATT

TATGATGTCAGTAAGCGGCCCTCAGGGATTTCTTTTCGCTTCTCTGGCTC

CAAGTCTGGCAACACGGCCTCCCTGACCATCTCTGGGCTCCAGGCTGAGG

ACGAGGCTGATTATTACTGCAGCTCATATACAAGTAACATGACCCCCTAT

GTCTTCGGCACTGGGACCAAGGTCACCGTCCTA 2.2.3 the Amino Acid Sequence of Each Heavy Chain Variable Region of O21 scFv is:

(SEQ ID NO: 40)
QVQLQQSGPGLVKPSQTLSLTCAISGDSVSSNSVSWDWIRQSPSRGLEWL

GRTYYRSKWYNEYAVSVESRITINPDTSKNQFSLQLNSVTPEDTAIYFCV

RNNYFFDLWGRGTLVTVSS where the underlined parts are CDR1, CDR2 and CDR3, respectively, with the sequence numbers of SEQ ID NOs: 41-43, respectively; the parts without underline are FR1, FR2, FR3 and FR4, respectively, with the sequence numbers of SEQ ID NOs:44-47, respectively.

The DNA sequence corresponding to the amino acid sequence of each heavy chain variable region of O21 scFv is:

(SEQ ID NO: 48)
CAGGTACAGCTGCAGCAGTCAGGTCCAGGACTGGTGAAGCCCTCGCAGAC

CCTCTCACTCACCTGTGCCATCTCCGGGGACAGTGTCTCTAGCAACAGTG

TCTCTTGGGACTGGATCAGGCAGTCCCCCTCGAGGGGCCTTGAGTGGCTG

GGAAGGACATACTATAGGTCCAAGTGGTATAATGAGTATGCAGTATCTGT

GGAAAGTCGAATAACCATCAACCCAGACACATCCAAGAACCAGTTCTCCC

TGCAACTGAACTCTGTGACTCCCGAGGACACGGCTATATATTTCTGTGTA

AGAAATAACTACTTCTTCGATCTCTGGGGCCGTGGTACCCTGGTCACCGT

CTCCTCA

The amino acid sequence of each light chain variable region of O21 scFv is:

(SEQ ID NO: 49)
EIVLTQSPATLSLSPGERATLSCRASQSVSSYLAWYQQKPGQAPRLLIYD

ASDRATGIPARFSGSGSGTDFTLTISSLEPEDFAVYYCQLRSNWPPGYTF

GQGTKVEIK where the underlined parts are CDR1, CDR2 and CDR3, respectively, with the sequence numbers of SEQ ID NOs: 50-52, respectively; the parts without underline are FR1, FR2, FR3 and FR4, respectively, with the sequence numbers of SEQ ID NOs:53-56, respectively.

The DNA sequence corresponding to the amino acid sequence of each light chain variable region of O21 scFv is:

(SEQ ID NO: 57)
GAAATTGTGTTGACACAGTCTCCAGCCACCCTGTCTTTGTCTCCAGGGGA

AAGAGCCACCCTCTCCTGCAGGGCCAGTCAGAGTGTTAGCAGCTACTTAG

CCTGGTACCAACAGAAACCTGGCCAGGCTCCCAGGCTCCTCATCTATGAT

GCATCCGACAGGGCCACTGGCATCCCAGCCAGGTTCAGTGGCAGTGGGTC

TGGGACAGACTTCACTCTCACCATCAGCAGCCTTGAGCCTGAAGATTTTG

CAGTTTATTACTGTCAGCTGCGTAGCAACTGGCCTCCGGGGTACACTTTT

GGCCAGGGGACCAAGGTGGAGATCAAA

Embodiment 3: scFv Antibodies of the Three Antibodies were Formatted as IgG-Type Antibodies The amino acid sequence of human IgG4 constant region was obtained based on the amino acid sequence (P01861) of the constant region of human immunoglobulin gamma4 (IgG4) in Uniprot protein database. The gene sequences of the heavy chain variable region of the VH sequences of the screened O3, O19, O21 and the gene sequences of the human IgG4 constant region were spliced together, respectively, and the spliced genes were synthesized and double-digested with HindIII and EcoRI (Fermentas) and subcloned into the vector pcDNA4/myc-HisA to obtain pcDNA4-O21HC, pcDNA4-O3HC, pcDNA4-O19HC.

The amino acid sequence of human K light constant region was obtained based on the amino acid sequence (P01834) of the κ constant region of human immunoglobulin in Uniprot protein database. The gene sequence of the light chain variable region of the VL sequences of the screened O21 and the gene sequence of human λ light chain constant region were spliced together; The amino acid sequence of human λ light constant region was obtained based on the amino acid sequence (A0M8Q6) of the λ constant region of human immunoglobulin in Uniprot protein database; The gene sequences of the heavy chain variable region of the VL sequences of the screened O3, O19 and the gene sequence of human light λ chain constant region were spliced together, respectively, and the spliced genes were synthesized and double-digested with HindIII and EcoRI (Fermentas) and subcloned into the vector pcDNA4/myc-HisA to obtain pcDNA4-O21LC, pcDNA4-O3LC, pcDNA4-O19LC.

Plasmids comprising the heavy or light chain obtained above were extracted using the plasmid maxi preparation kit (PL14) supplied by AidLab. Recombinant plasmids comprising the heavy or light chain were co-transfected into HEK293 cells for antibody expression. The recombinant expression plasmids were diluted with FreeStyle293 medium and PEI (polyethylenimine) solution for transformation; each group of plasmid/PEI mixture was added to the cell suspension respectively and incubated at 37° C., 10% CO2 and 120 rpm; after 5-6 days, the transient expression culture supernatant was collected and purified by Protein A affinity chromatography to obtain anti-hOX40 antibodies: O3mAb, O19mAb and O21mAb.

Embodiment 4: Identification of Anti-hOX40Abs

Identification of Whether the Antibodies Specifically Recognize hOX40:

Binding of Purified Anti-hOX40 Antibodies to hOX40, hCD137 and hCD27 Proteins

Figure 2:
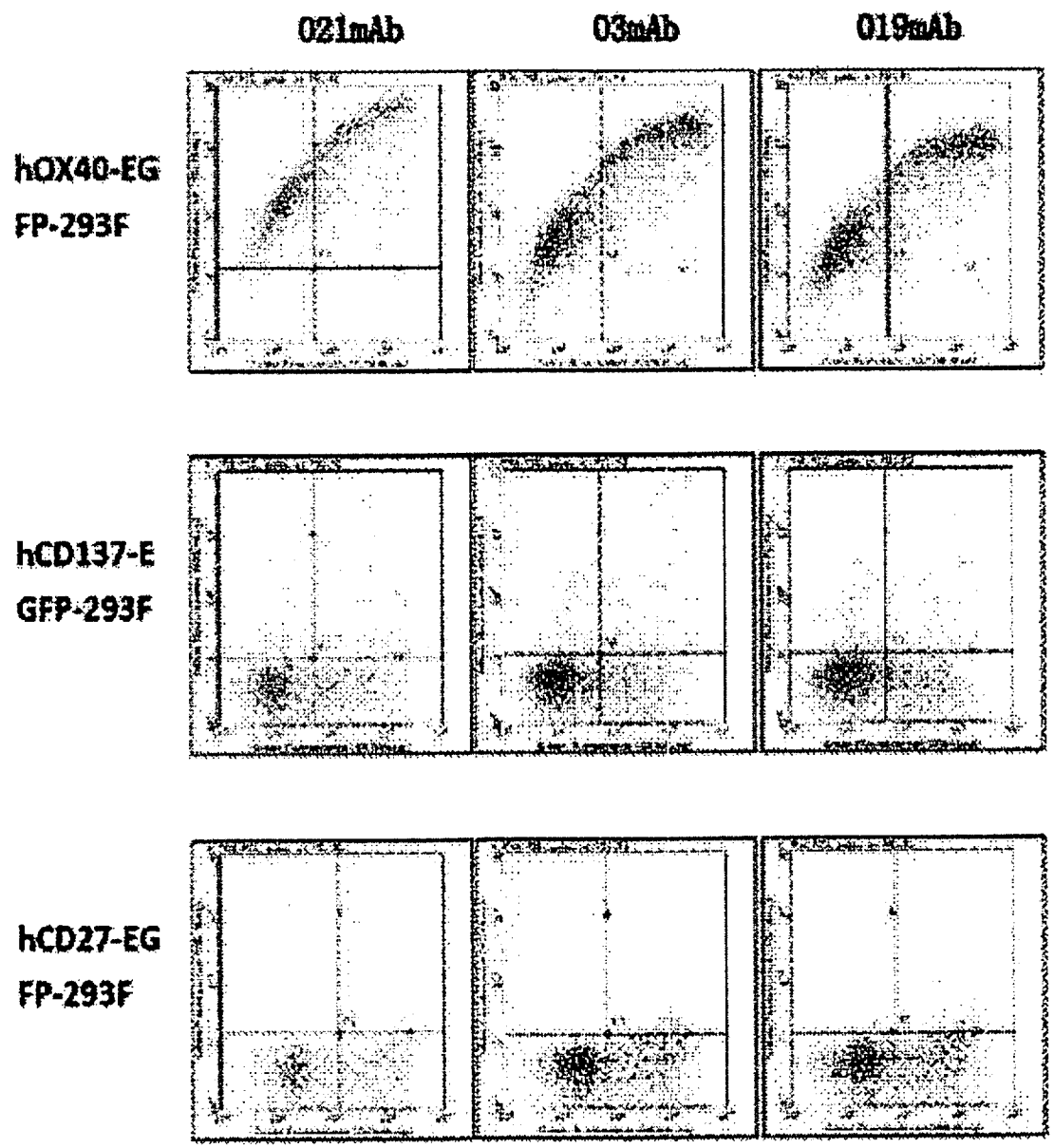
FIG. 2 shows antibody specificity detection of the anti-OX40, where the x-axis indicates the fluorescence intensity of EGFP and the y-axis indicates the fluorescence intensity of anti-hIg-PE.

HEK293 cells expressing hOX40-EGFP, hCD137-EGFP and hCD27-EGFP obtained in Embodiment 1 were resuspended in 0.5% PBS-BSA Buffer and anti-hOX40 mAb protein was added and the mixture was incubated on ice for 20 min. After washing, secondary antibody anti-hIg-PE (eBioscience) was added, and the mixture was incubated on ice for 20 min. After washing, the cells were resuspended in 500 μl 0.5% PBS-BSA Buffer and detected by flow cytometry. As shown in FIG. 2, all the three antibodies (O3mAb, O19mAb and O21mAb) can bind to hOX40-EGFP cells but not to several other EGFP cells (hCD137-RGFP-293F, hCD27-RGFP-293F) and very good specificity was shown.

Embodiment 5: Increased In Vitro Affinity of Anti-OX40 Antibody

Since all the three antibodies (O3mAb, O19mAb and O21mAb) were able to specifically bind to hOX40-EGFP cells and O21 scFv was found to have a higher affinity to hOX40 with a stable higher expression level by transient transfection, therefore O21 scFv antibody was selected for further in vitro affinity test. However, it should be noted that the purpose of the in vitro affinity test is to study the influence of the mutation rate on the antibody affinity. The test result should not be limited to the identification of O21 scFv but should be understood as the influence of the mutation rate on the affinity of antibodies including O3 scFv, O19 scFv and O21 scFv.

5.1 Construction of Yeast Library of Anti-OX4021 # ScFv with Improved Affinity

The standard PCR reaction was performed using the pcDNA4-OX40-21-Fc plasmid constructed in Embodiment 1 as a template, pcDNA4-F:TCTGGTGGTGGTGGTTCT-GCTAGC (SEQ ID NO: 58) and cMyc-BBXhoI: GCCA-GATCTCGAGCTATTACAAGTCTTCTTCA-GAAATAAGCTTTTGTTCTAGAATTCCG (SEQ ID NO: 59) as primers. The resulting PCR products were digested with NheI and BglII from Fermentas to construct a recombinant plasmid. Next, a random mutation PCR product of scFv was obtained by error prone PCR using the method of Ginger et al. (2006) Nat Protoc 1 (2): 755-68. The primers used were ep-F: TAATACGACTCACTATAGGG (SEQ ID NO: 60) and ep-R: GGCAGCCCCATAAACACACAGTAT (SEQ ID NO: 61). The resulting PCR products were purified by the GeneJET DNA purification Kit from Fermentas and then precipitated in ethanol to a concentration greater than 1 μg/μl. The remainder of the procedure references the method of Ginger et al. (2006) Nat Protoc 1 (2): 755-68 to obtain an affinity-matured yeast library using yeast electrotransformation and in vivo recombination.

5.2 Screening of Yeasts Expressing Anti-OX40 21 # scFv with Improved Affinity

The affinity-matured yeast library obtained above was subjected to two rounds of FACS with 10 nM and 1 nM hOX40-Fc protein, and the resulting yeast products were plated and subjected to monoclonal identification. The yeast monoclones expressing antibodies with improved affinity were identified by flow cytometry using the method of staining with low concentration of antigen and the wild-type yeast obtained previously as a control. The yeast colonies identified by FACS were subjected to yeast colony PCR and sequencing as above. The obtained sequences were sequenced and analyzed using BioEdit software for mutation sites.

Figure 3:
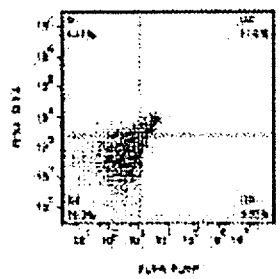
FIG. 3 is a graph showing the staining results of yeast monoclones expressing antibodies with improved affinity.
Figure 3:
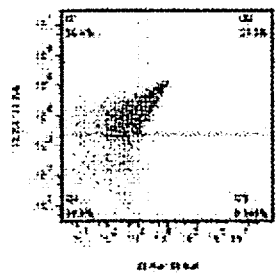
Figure 3:
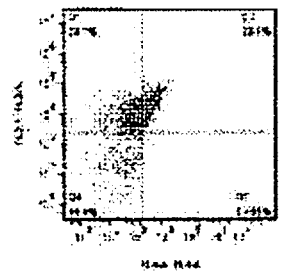
Figure 3:
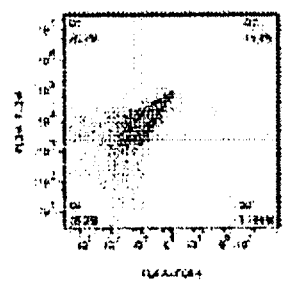
Figure 3:
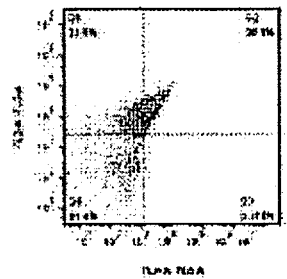
Figure 3:
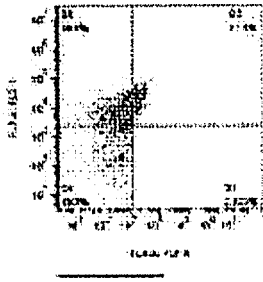
Figure 3:
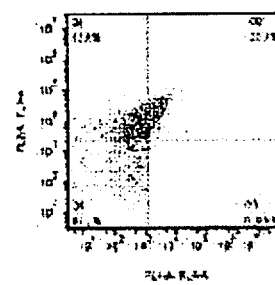
Figure 3:
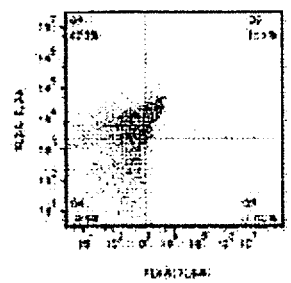
Figure 3:
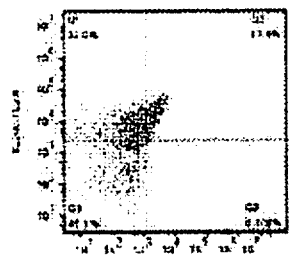

The mutation sites in O21 scFv that did not affect or even improve antibody affinity are shown in Table 1. The results in this table shows that one or more of the mutations in O21 scFv set forth in the table do not affect or even improve affinity; the results of corresponding sequence analysis for selected yeast monoclones are shown in Table 2. This table shows that the mutation sites listed in Table 1, when combined as shown in Table 2, can improve the affinity of the antibody. The staining results of the yeasts shown in Table 2 are shown in FIG. 3, and compared with O21 scFv, the affinity of the antibody has been improved to varying degrees.

TABLE 1

Mutation sites in O21 scFv with no effect on antibody affinity

| Heavy chain | Light chain |
|---|---|
| Position H7: S mutated to L | Position L30: S mutated to G |
| Position H13: K mutated to M | Position L90: L mutated to Q |

TABLE 1-continued

Mutation sites in O21 scFv with no effect on antibody affinity

| Heavy chain | Light chain |
|---|---|
| Position H28: S mutated to N | |
| Position H33: S mutated to G | |
| Position H43: R mutated to G | |
| Position H65: S mutated to N | |
| Position H67: I mutated to M | |
| Position H96: N mutated to D | |

TABLE 2

The results of sequence analysis for yeast monoclones expressing antibodies with improved affinity;

| Name | Mutation site (heavy chain) | Mutation site (light chain) |
|---|---|---|
| anti-OX40-21-1 | | Position L90: L mutated to Q |
| anti-OX40-21-2 | Position H43: R mutated to G | |
| | Position H96: N mutated to D | |
| anti-OX40-21-7 | | Position L30: S mutated to G |
| | | Position L90: L mutated to Q |
| anti-OX40-21-11 | Position H7: S mutated to L | Position L30: S mutated to G |
| | Position H96: N mutated to D | |
| anti-OX40-21-13 | Position H28: S mutated to N | |
| | Position H33: S mutated to G | |
| | Position H96: N mutated to D | |
| anti-OX40-21-14 | Position H96: N mutated to D | Position L30: S mutated to G |
| anti-OX40-21-16 | Position H67: I mutated to M | Position L90: L mutated to Q |
| anti-OX40-21-17 | Position H13: K mutated to M | |
| | Position H65: S mutated to N | |
| | Position H96: N mutated to D | |

From Table 2, it has been experimentally shown that the affinity of the antibody can still be maintained or even improved if 3 and 2 amino acids in the heavy chain CDRs and the light chain CDRs of O21 scFv are mutated, respectively (up to 3 amino acids can be mutated in the anti-OX40 21 # H96-L80 mAb in Embodiment 6). It is now known that the heavy chain variable regions and the light chain variable regions of O21 scFv comprise 119 amino acids (wherein the CDRs contain 32 amino acids, the FRs contain 87 amino acids) and 109 amino acids (wherein the CDRs contain 29 amino acids and the FRs contain 80 amino acids), then it can be considered that an antibody with more than 90% homology with the heavy chain CDRs or the light chain CDRs still have the ability to maintain or even improve the affinity of the antibody. In practice, the affinity of an antibody has no decisive relationship with the percentage of sequence homology, but rather affected by the key amino acid residues that constitute the epitope (or antigenic determinant). The sequence homology can be as low as 70% if these key amino acid residues have not been mutated or the mutations thereof do not have played a decisive role in the affinity change.

Embodiment 6: scPv Antibodies were Formatted as IgG-Type Antibodies

Affinity-matured scFv antibodies were formatted as IgG type antibodies according to the method in Embodiment 3 to obtain a series of anti-OX40 21 # mAb variants with the following sequence:

6.1 Anti-OX40 21#H28H33 mAb

The amino acid sequence of the heavy variable region of anti-OX40 21#H28H33 mAb is:

(SEQ ID NO: 62)
QVQLQQSGPGLVKPSQTLSLTCAISGD<u>N</u>VSS<u>NG</u>VSWDWIRQSPSRGLE

WLG<u>RTYYRSKWYNEYAVSVES</u>RITINPDTSKNQFSLQLNSVTPEDTAIY

FCVR<u>NNYFFDL</u>WGRGTLVTVSS where the underlined parts are CDR1, CDR2 and CDR3, respectively, (the parts in the box are the mutated parts), with the sequence numbers of SEQ ID NOs:63, 42 and 43, respectively; the parts without underline are FR1, FR2, FR3 and FR4, respectively, with the sequence numbers of SEQ ID NOs:64, 45, 46 and 47, respectively.

The DNA sequence corresponding to the amino acid sequence of the heavy variable region of anti-OX40 21#H28H33 mAb is:

(SEQ ID NO: 65)
CAGGTACAGCTGCAGCAGTCAGGTCCAGGACTGGTGAAGCCCTCGCAGA

CCCTCTCACTCACCTGTGCCATCTCCGGGGAC<u>AAT</u>GTCTCTAGCAAC<u>GG</u>

<u>T</u>GTCTCTTGGGACTGGATCAGGCAGTCCCCCTCGAGGGGCCTTGAGTG

GCTGGGAAGGACATACTATAGGTCCAAGTGGTATAATGAGTATGCAGTA

TCTGTGGAAAGTCGAATAACCATCAACCCAGACACATCCAAGAACCAGT

TCTCCCTGCAACTGAACTCTGTGACTCCCGAGGACACGGCTATATATTT

CTGTGTAAGAAATAACTACTTCTTCGATCTCTGGGGCCGTGGTACCCTG

GTCACCGTCTCCTCA

The amino acid sequence of the light variable region of anti-OX40 21#H28H33 mAb is:

(SEQ ID NO: 49)
EIVLTQSPATLSLSPGERATLSC<u>RASQSVSSYLA</u>WYQQKPGQAPRLLIY<u>D</u>

<u>ASDRAT</u>GIPARFSGSGSGTDFTLTISSLEPEDFAVYYC<u>QLRSNWPPGYT</u>F

GQGTKVEIK where the underlined parts are CDR1, CDR2 and CDR3, respectively, with the sequence numbers are SEQ ID NOs: 50-52, respectively; the parts without underline are FR1, FR2, FR3 and FR4, respectively, with the sequence numbers are SEQ ID NOs: 53-56, respectively.

The DNA sequence corresponding to the amino acid sequence of the light variable region of anti-OX40 21#H28H33 mAb is:

(SEQ ID NO: 57)
GAAATTGTGTTGACACAGTCTCCAGCCACCCTGTCTTTGTCTCCAGGGGA

AAGAGCCACCCTCTCCTGCAGGGCCAGTCAGAGTGTTAGCAGCTACTTAG

CCTGGTACCAACAGAAACCTGGCCAGGCTCCCAGGCTCCTCATCTATGAT

GCATCCGACAGGGCCACTGGCATCCCAGCCAGGTTCAGTGGCAGTGGGTC

TGGGACAGACTTCACTCTCACCATCAGCAGCCTTGAGCCTGAAGATTTTG

CAGTTTATTACTGTCAGCTGCGTAGCAACTGGCCTCCGGGGTACACTTTT

GGCCAGGGGACCAAGGTGGAGATCAAA 6.2 Anti-OX40 21#H65 mAb

The amino acid sequence of the heavy chain variable region of anti-OX40 21#H65 mAb is:

(SEQ ID NO: 66)
QVQLQQSGPGLVKPSQTLSLTCAISGDSVSSNSVSWDWIRQSPSRGLEW

LGRTYYRSKWYNEYAVSVENRITINPDTSKNQFSLQLNSVTPEDTAIYF

CVRNNYFFDLWGRGTLVTVSS where the underlined parts are CDR1, CDR2 and CDR3, respectively, (the parts in the box are the mutated parts), with the sequence numbers of SEQ ID NOs:41, 67 and 43, respectively; the parts without underline are FR1, FR2, FR3 and FR4, respectively, with the sequence numbers of SEQ ID NOs:44-47, respectively.

The DNA sequence corresponding to the amino acid sequence of the heavy chain variable region of anti-OX40 21#H65 mAb is:

(SEQ ID NO: 68)
CAGGTACAGCTGCAGCAGTCAGGTCCAGGACTGGTGAAGCCCTCGCAGA

CCCTCTCACTCACCTGTGCCATCTCCGGGGACAGTGTCTCTAGCAACAG

TGTCTCTTGGGACTGGATCAGGCAGTCCCCCTCGAGGGGCCTTGAGTGG

CTGGGAAGGACATACTATAGGTCCAAGTGGTATAATGAGTATGCAGTAT

CTGTGGAAAATCGAATAACCATCAACCCAGACACATCCAAGAACCAG

TTCTCCCTGCAACTGAACTCTGTGACTCCCGAGGACACGGCTATATATT

TCTGTGTAAGAAATAACTACTTCTTCGATCTCTGGGGCCGTGGTACCCT

GGTCACCGTCTCCTCA

The amino acid sequence of the light chain variable region of anti-OX40 21#H65 mAb is:

(SEQ ID NO: 49)
EIVLTQSPATLSLSPGERATLSCRASQSVSSYLAWYQQKPGQAPRLLIYD

ASDRATGIPARFSGSGSGTDFTLTISSLEPEDFAVYYCQLRSNWPPGYTF

GQGTKVEIK where the underlined parts are CDR1, CDR2 and CDR3, respectively, with the sequence numbers of SEQ ID NOs: 50-52, respectively; the parts without underline are FR1, FR2, FR3 and FR4, respectively, with the sequence numbers of SEQ ID NOs:53-56, respectively.

The DNA sequence corresponding to the amino acid sequence of the light chain variable region of anti-OX40 21#H65 mAb is:

(SEQ ID NO: 57)
GAAATTGTGTTGACACAGTCTCCAGCCACCCTGTCTTTGTCTCCAGGGGA

AAGAGCCACCCTCTCCTGCAGGGCCAGTCAGAGTGTTAGCAGCTACTTAG

CCTGGTACCAACAGAAACCTGGCCAGGCTCCCAGGCTCCTCATCTATGAT

GCATCCGACAGGGCCACTGGCATCCCAGCCAGGTTCAGTGGCAGTGGGTC

TGGGACAGACTTCACTCTCACCATCAGCAGCCTTGAGCCTGAAGATTTTG

CAGTTTATTACTGTCAGCTGCGTAGCAACTGGCCTCCGGGGTACACTTTT

GGCCAGGGGACCAAGGTGGAGATCAAA 6.3 Anti-OX40 21#H96 mAb

The amino acid sequence of the heavy chain variable region of anti-OX40 21#H96 mAb is:

(SEQ ID NO: 69)
QVQLQQSGPGLVKPSQTLSLTCAISGDSVSSNSVSWDWIRQSPSRGLEW

LGRTYYRSKWYNEYAVSVESRITINPDTSKNQFSLQLNSVTPEDTAIYF

CVRNDYFFDLWGRGTLVTVSS where the underlined parts are CDR1, CDR2 and CDR3, respectively, (the parts in the box are the mutated parts), with the sequence numbers of SEQ ID NOs:41, 42 and 70, respectively; the parts without underline are FR1, FR2, FR3 and FR4, respectively, with the sequence numbers of SEQ ID NOs:44-47, respectively.

The DNA sequence corresponding to the amino acid sequence of the heavy chain variable region of anti-OX40 21#H96 mAb is:

(SEQ ID NO: 71)
CAGGTACAGCTGCAGCAGTCAGGTCCAGGACTGGTGAAGCCCTCGCAGA

CCCTCTCACTCACCTGTGCCATCTCCGGGGACAGTGTCTCTAGCAACAG

TGTCTGGGACTGGATCAGGCAGTCCCCCTCGAGGGGCCTTGAGTGGCTG

GGAAGGACATACTATAGGTCCAAGTGGTATAATGAGTATGCAGTATCTG

TGGAAAGTCGAATAACCATCAACCCAGACACATCCAAGAACCAGTTCTC

CCTGCAACTGAACTCTGTGACTCCCGAGGACACGGCTATATATTTCTGT

GTAAGAAATGACTACTTCTTCGATCTCTGGGGCCGTGGTACCCTGGTCA

CCGTCTCCTCA

The amino acid sequence of the light chain variable region of anti-OX40 21#H96 mAb is:

(SEQ ID NO: 49)
EIVLTQSPATLSLSPGERATLSCRASQSVSSYLAWYQQKPGQAPRLLIYD

ASDRATGIPARFSGSGSGTDFTLTISSLEPEDFAVYYCQLRSNWPPGYTF

GQGTKVEIK where the underlined parts are CDR1, CDR2 and CDR3, respectively, with the sequence numbers of SEQ ID NOs: 50-52, respectively; the parts without underline are FR1, FR2, FR3 and FR4, respectively, with the sequence numbers of SEQ ID NOs:53-56, respectively.

The DNA sequence corresponding to the amino acid sequence of the light chain variable region of anti-OX40 21#H96 mAb is:

(SEQ ID NO: 57)
GAAATTGTGTTGACACAGTCTCCAGCCACCCTGTCTTTGTCTCCAGGGGA

AAGAGCCACCCTCTCCTGCAGGGCCAGTCAGAGTGTTAGCAGCTACTTAG

CCTGGTACCAACAGAAACCTGGCCAGGCTCCCAGGCTCCTCATCTATGAT

GCATCCGACAGGGCCACTGGCATCCCAGCCAGGTTCAGTGGCAGTGGGTC

TGGGACAGACTTCACTCTCACCATCAGCAGCCTTGAGCCTGAAGATTTTG

CAGTTTATTACTGTCAGCTGCGTAGCAACTGGCCTCCGGGGTACACTTTT

GGCCAGGGGACCAAGGTGGAGATCAAA 6.4 Anti-OX40 21#VHnew-L80

The amino acid sequence of the heavy chain variable region of anti-OX40 21#VHnew-L80 is:

(SEQ ID NO: 72)
QVQLQQSGPGLVICPSQTLSLTCAISGDSVSSN̄GVSWDWIRQSPSRGLE

WLGRTYYRSKWYNEYAVSVEN̄RITINPDTSKNQFSLQLNSVTPEDTAIY

FCVRND̄YFFDLWGRGTLVTVSS

The underlined parts are CDR1, CDR2 and CDR3, respectively, (the parts in the box are the mutated parts), with the sequence numbers of SEQ ID NOs:63, 67 and 70, respectively; the parts without underline are FR1, FR2, FR3 and FR4, respectively, with the sequence numbers of SEQ ID NOs:44-47, respectively;

The DNA sequence corresponding to the amino acid sequence of the heavy chain variable region of anti-OX40 21#VHnew-L80 is:

(SEQ ID NO: 73)
CAGGTACAGCTGCAGCAGTCAGGTCCAGGACTGGTGAAGCCCTCGCAGA

CCCTCTCACTCACCTGTGCCATCTCCGGGGACAGTGTCTCTAGCAACGG

TGTCTCTTGGGACTGGATCAGGCAGTCCCCCTCGAGGGGCCTTGAGTGG

CTGGGAAGGACATACTATAGGTCCAAGTGGTATAATGAGTATGCAGTAT

CTGTGGAAAATCGAATAACCATCAACCCAGACACATCCAAGAACCAG

TTCTCCCTGCAACTGAACTCTGTGACTCCCGAGGACACGGCTATATATT

TCTGTGTAAGAAATGACTACTTCTTCGATCTCTGGGGCCGTGGTACCC

TGGTCACCGTCTCCTCA

The amino acid sequence of the light chain variable region of anti-OX40 21#VHnew-L80 is:

(SEQ ID NO: 74)
EIVLTQSPATLSLSPGERATLSCRASQSVGSYLAWYQQKPGQAPRLLIY

DASN̄RATGIPARFSGSGSGTDFTLTISSLEPEDFAVYYCQQRSNWPPGY

TFGQGTKVEIK where the underlined parts are CDR1, CDR2 and CDR3, respectively, (the parts in the box are the mutated parts), with the sequence numbers of SEQ ID NOs:75-77, respectively; the parts without underline are FR1, FR2, FR3 and FR4, respectively, with the sequence numbers thereof are SEQ ID NOs:53-56, respectively;

The DNA sequence corresponding to the amino acid sequence of the light chain variable region of anti-OX40 21#VHnew-L80 is:

(SEQ ID NO: 78)
GAAATTGTGTTGACACAGTCTCCAGCCACCCTGTCTTTGTCTCCAGGGG

AAAGAGCCACCCTCTCCTGCAGGGCCAGTCAGAGTGTTGGCAGCTAC

TTAGCCTGGTACCAACAGAAACCTGGCCAGGCTCCCAGGCTCCTCATCT

ATGATGCATCCAACAGGGCCACTGGCATCCCAGCCAGGTTCAGTGGCAG

TGGGTCTGGGACAGACTTCACTCTCACCATCAGCAGCCTTGAGCCTGAA

GATTTTGCAGTTTATTACTGTCAGCAGCGTAGCAACTGGCCTCCGGGGT

ACACTTTTGGCCAGGGGACCAAGGTGGAGATCAAA 6.5 Anti-OX40 21#H96-L80mAb

The amino acid sequence of the heavy chain variable region of anti-OX40 21#H96-L80mAb is:

(SEQ ID NO: 79)
QVQLQQSGPGLVKPSQTLSLTCAISGDSVSSNSVSWDWIRQSPSRGLE

WLGRTYYRSKWYNEYAVSVESRITINPDTSKNQFSLQLNSVTPEDTAI

YFCVRND̄YFFDLWGRGTLVTVSS where the underlined parts are CDR1, CDR2 and CDR3, respectively, (the parts in the box are the mutated parts), with the sequence numbers of SEQ ID NOs:41, 42 and 70, respectively; the parts without underline are FR1, FR2, FR3 and FR4, respectively, with the sequence numbers of SEQ ID NOs:44-47, respectively;

The DNA sequence corresponding to the amino acid sequence of the heavy chain variable region of anti-OX40 21#H96-L80mAb is:

(SEQ ID NO: 80)
CAGGTACAGCTGCAGCAGTCAGGTCCAGGACTGGTGAAGCCCTCGCAGA

CCCTCTCACTCACCTGTGCCATCTCCGGGGACAGTGTCTCTAGCAACAG

TGTCTCTTGGGACTGGATCAGGCAGTCCCCCTCGAGGGGCCTTGAGTGG

CTGGGAAGGACATACTATAGGTCCAAGTGGTATAATGAGTATGCAGTAT

CTGTGGAAAGTCGAATAACCATCAACCCAGACACATCCAAGAACCAGTT

CTCCCTGCAACTGAACTCTGTGACTCCCGAGGACACGGCTATATATTTC

TGTGTAAGAAATGACTACTTCTTCGATCTCTGGGGCCGTGGTACCCTGG

TCACCGTCTCCTCA

The amino acid sequence of the light chain variable region of anti-OX40 21#H96-L80mAb is:

(SEQ ID NO: 74)
EIVLTQSPATLSLSPGERATLSCRASQSVGSYLAWYQQKPGQAPRLLI

YDASNRATGIPARFSGSGSGTDFTLTISSLEPEDFAVYYCQQRSNWPP

GYTFGQGTKVEIK where the underlined parts are CDR1, CDR2 and CDR3, respectively, (the parts in the box are the mutated parts), with the sequence numbers of SEQ ID NOs:75-77, respectively; the parts without underline are FR1, FR2, FR3 and FR4, respectively, with the sequence numbers of SEQ ID NOs: 53-56, respectively;

The DNA sequence corresponding to the amino acid sequence of the light chain variable region of anti-OX40 21#H96-L80mAb is:

(SEQ ID NO:78)
GAAATTGTGTTGACACAGTCTCCAGCCACCCTGTCTTTGTCTCCAGGGG

AAAGAGCCACCCTCTCCTGCAGGGCCAGTCAGAGTGTTGGCAGCTACTT

AGCCTGGTACCAACAGAAACCTGGCCAGGCTCCCAGGCTCCTCATCTAT

GATGCATCCAACAGGGCCACTGGCATCCCAGCCAGGTTCAGTGGCAGTG

GGTCTGGGACAGACTTCACTCTCACCATCAGCAGCCTTGAGCCTGAAGA

TTTTGCAGTTTATTACTGTCAGCAGCGTAGCAACTGGCCTCCGGGGTAC

ACTTTGGCCAGGGGACCAAGGTGGAGATCAAA

Figure 4:
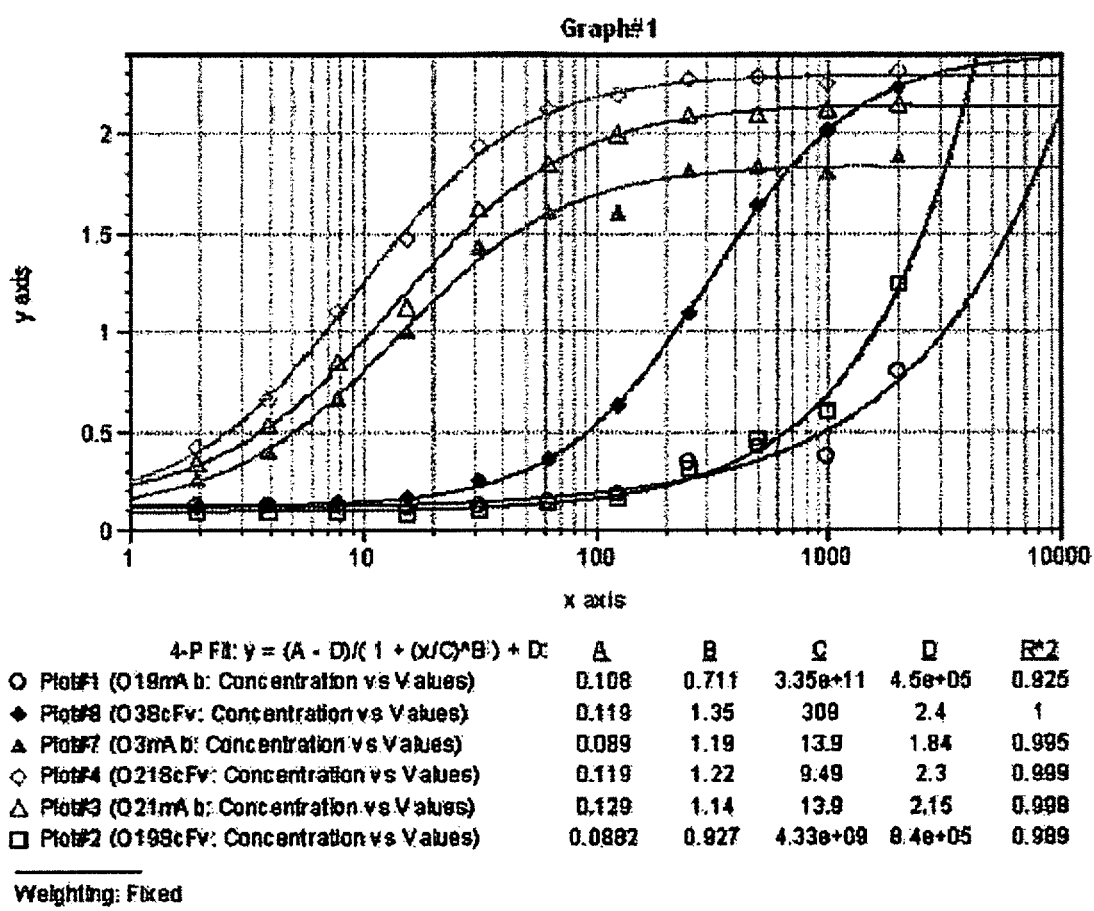
FIG. 4 is a graph showing the binding capacity of three antibodies to hOX40 using ELISA detection.
Figure 5:
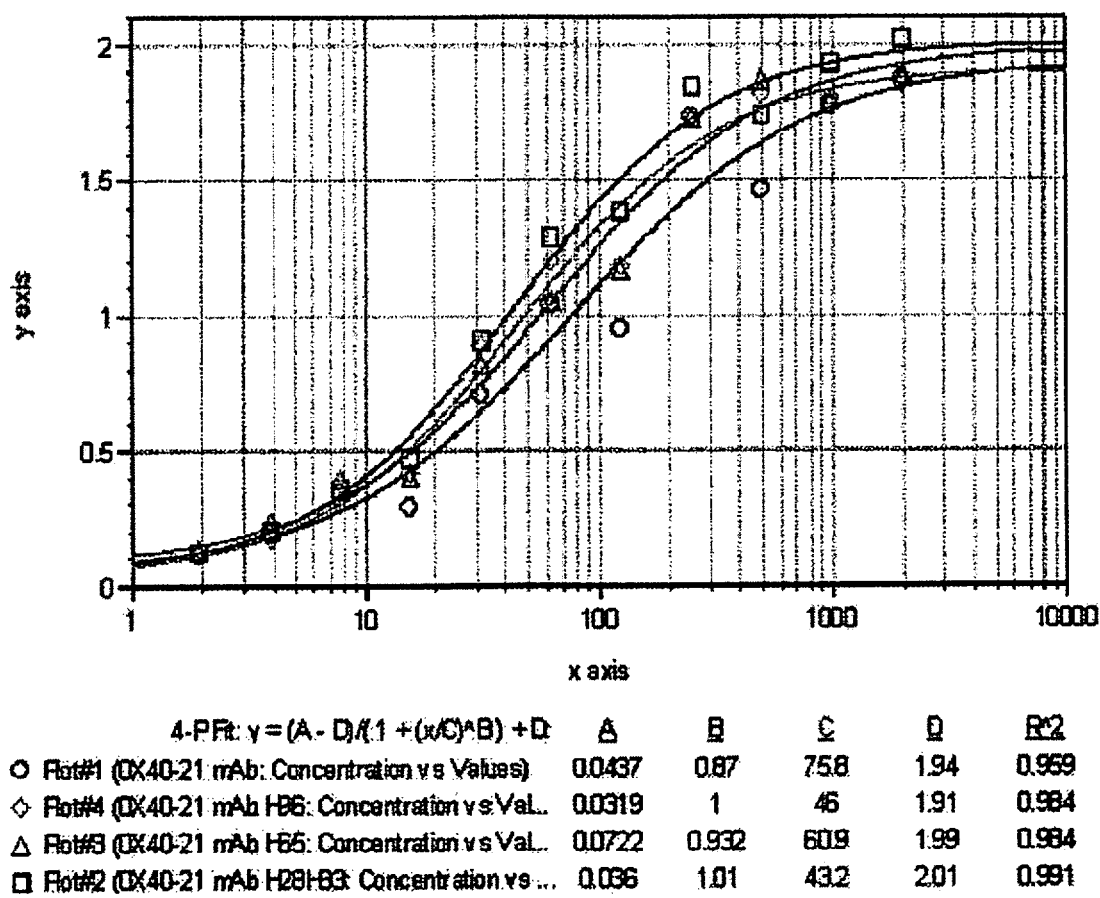
FIG. 5 is a graph showing the binding capacity of different heavy chain mutants to hOX40 after affinity maturation using ELISA detection.
Figure 6:
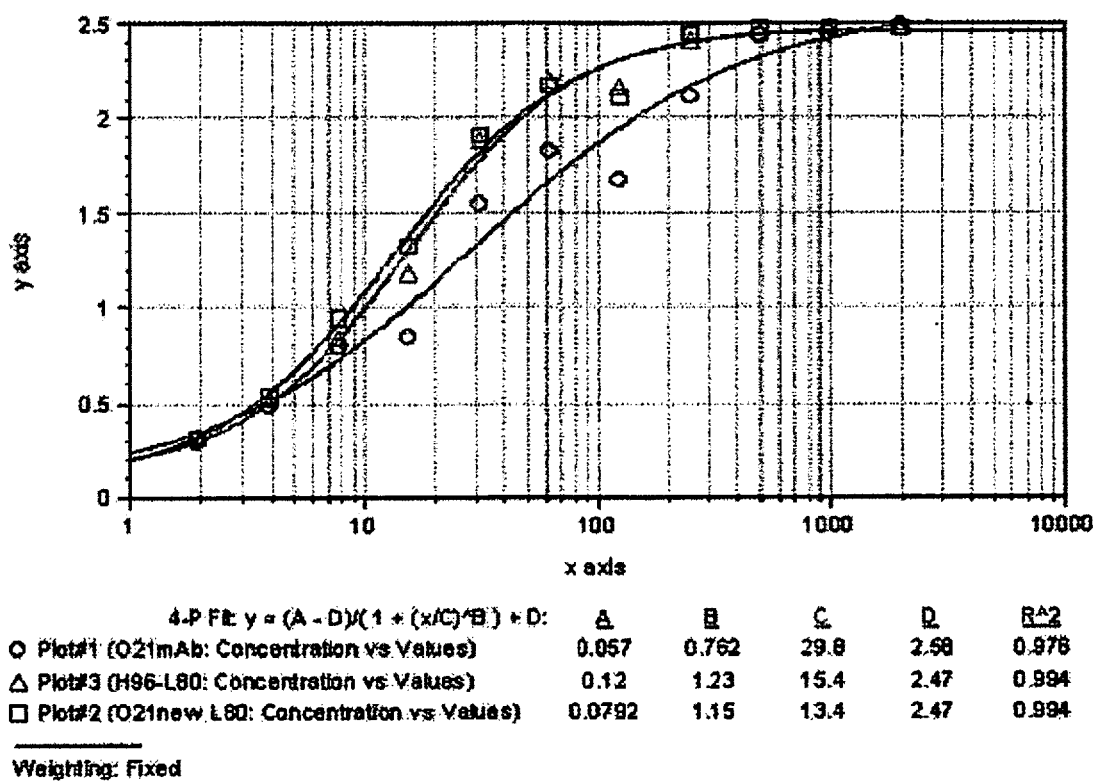
FIG. 6 is a graph showing the binding capacity of H96 heavy chain mutant and different light chain mutants to hOX40 after affinity maturation using ELISA detection.

Embodiment 7: Identification of Anti-hOX40 Abs 7.1 Binding Affinity Test of Purified Anti-hOX40 Antibody to hOX40 (ELISA)

hOX40-muFc was diluted to 2 μg/ml with coating buffer (50 mM $Na_2CO_3$, $NaHCO_3$ pH 9.6), 100 μL/well, 4° C. overnight. After washing, blocking was performed using 3% BSA-PBS for 1 h at 37° C. The anti-hOX40 antibodies were diluted respectively from 2000 ng/ml and was diluted 2-fold in a total of 11 concentrations, with the diluent (1% BSA-PBS) as a control, and incubated at 37° C. for 2 h. Goat anti-human IgG-HRP conjugated was added and incubated for 1 h at 37° C. Soluble one-component TMB substrate developer solution is added, and the developing was performed in dark at room temperature for 5-10 min. 2N $H_2SO_4$ 50 μL/well was added to terminate the color development reaction. The OD of the obtained solution was determined at 450 nm-650 nm on MD SpectraMax Plus 384 microplate reader and SoftMaxPro v5.4 was used for processing data, making graphs and analysis. The results are shown in FIGS. 4-6. It can be seen from FIG. 4 that the affinity of O19 mAb remains relatively low after the conversion from ScFv to IgG-type antibody; the affinity of O21 mAb does not change much and is good; and the affinity of O3 mAb is significantly improved. It can be seen from FIG. 5 and FIG. 6 that all the above variants of anti-OX40 21 # mAb can bind to OX40 and the affinity of the in vitro affinity-matured anti-OX40 21 # VHnew-L80 mAb and anti-OX40 21#H96-L80 mAb increased approximately two times compared to anti-OX40 21# mAb.

7.2 Analysis of Kinetic Affinity Constant of a-hOX40 mAbs to hOX40 by Surface Plasmon Resonance (SPR)

The binding kinetics of anti-hOX40 antibody to recombinant human OX40 was measured by surface plasmon resonance (SRP) method using a BIAcore X100 instrument. Anti-human Fc antibody (no cross-identification against the mouse Fc) was conjugated on CM5 chip, the test antibody was diluted to 5 nM with running buffer and captured as a ligand by the anti-human Fc antibody on the CM5 chip. OX40-muFc was diluted with running buffer to 1000-1.37 nM, in a 2-fold serial dilution factor. The injection time is 180 s, the dissociation time is 1800 s and the regeneration time is 60 s. The running buffer is HBS-EP+, and the regeneration buffer is 10 mM glycine-HCl (pH 2.0). The association rate ($k_{on}$) and dissociation rate ($k_{off}$) were calculated using a simple one-to-one Languir binding model (BIAcore Evaluation Software version 3.2). The equilibrium dissociation constant (kD) is calculated as the ratio $k_{off}/k_{on}$. It can be seen from Table 3 that the affinity of the affinity-matured anti-OX40 21 # H96-L80 mAb is increased approximately two times.

TABLE 3

Binding kinetic test of anti-hOX40 antibody to hOX40

| Name | Kon (1/Ms) | Koff (1/s) | KD (M) |
| --- | --- | --- | --- |
| O3 mAb | 2.84E+05 | 3.91E−04 | 1.378E−09 |
| O21 mAb | 4.181E+4 | 6.077E−04 | 1.454E−08 |
| VHnew-L80 | 3.329E+04 | 3.415E−04 | 1.026E−08 |
| H96-L80 | 2.999E+04 | 2.368E−04 | 7.898E−09 |

In Vitro Agonist Activity Detection of Anti-hOX40 Antibody by NF-κb System

Construction of OX40-CD40 plasmid: the amino acid sequences of the human OX40 extracellular domain and transmembrane domain (i.e., the residue 1 to the residue 235 in P43489) was obtained based on the amino acid sequence of human OX40 (P43489) in the Uniprot protein database; The amino acid sequence of the intracellular domain of human CD40 (i.e., the residue 216 to the residue 277 in P25942) was obtained based on the amino acid sequence of human CD40 (P25942) in the Uniprot protein database; The two amino acid sequences obtained above were spliced together via gene synthesis, then sub-cloned into the commercial vector pcDNA4/myc-HisA (Invitrogen, V863-20) by double digestion by HindIII and EcoRI (Fermentas), and the accuracy of the constructed plasmid was verified by sequencing to obtain recombinant plasmid DNA: pcDNA4-OX40-CD40 (i.e. OX40-CD40 mentioned below);

293T-NF-κB stable cell line: 293T cells were seeded in a 24-well plate ($1 \times 10^5$/well and 200 μl DMEM complete medium/well) with 20 μl NF-κB-luciferase-lentivirus (Qiagen, cat: CLS-013L) added, MOI=2. 24 h after infection, the supernatant was discarded and 1 ml of DMEM complete medium was added for continue culturing. After 24 h, the medium was replaced with DMEM complete medium containing 0.3 μg/ml of promycin for continue culturing, the cells were cultured, propagated and frozen for storage. The 293T-NF-κB cells screened by promycin were seeded in a 24-well plate ($1 \times 10^5$/well) and stimulated with 10 ng/ml TNF-α for 6 h. Then the cells were lysed and detected for luciferase. It showed that the luciferase values of TNF-α-stimulated cells were significantly higher than those of untreated cells, demonstrating that NF-κB-luciferase has been stably introduced into 293T cells via transgene.

Figure 7:
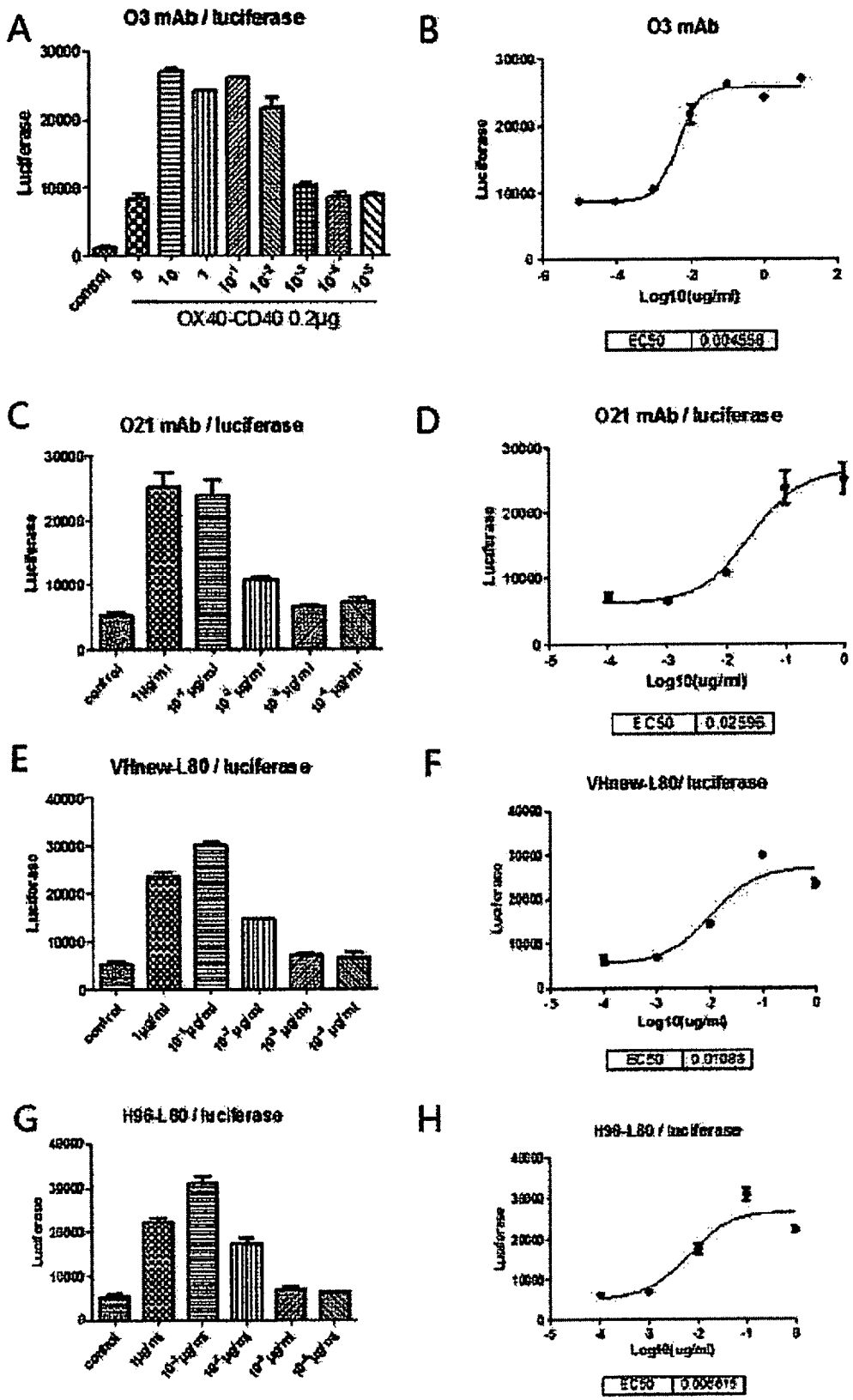
FIG. 7 is a graph showing the results of the in vitro agonist activity detection of anti-hOX40 antibodies.

$5 \times 10^5$ 293 T-NF-κB cells were resuspended in medium without double antibiotics and seeded in a 6-well plate. After 24 h, the supernatant was discarded and washed once with PBS. 1.8 ml of culture solution without double antibiotics and serum was added. 0.2 μg of OX40-CD40 plasmid was transfected in the ratio of plasmid:liposome=1:3. 4 h after transfection, the supernatant was discarded, replaced with fresh complete culture solution, and the culture was continued. One the day after transfection, the cells were seeded in a 96-well plate at a density of $5\times10^4$/well, and antibodies with a series of concentration gradients (initial concentration of 10 μg/ml, seven gradients through 10-fold dilutions) were added, at the same time, cross-link (Jackson ImmunoResearch Laboratories: 109-006-008) with the same concentration was added and the culture was continued for 6 h, then the cells were lysed and detected for luciferase. As shown in FIGS. 7, A, C, E and G represent the results of the in vitro agonist activity detection of O3 mAb, O21 mAb, anti-OX40 21 # VHnew-L80 mAb and anti-OX40 21 # H96-L80 mAb at different concentrations, respectively; B, D, F and H are the results of the in vitro agonist activity detection after logistic transformation, respectively. The results show that both O3 mAb and O21 mAb have good agonist activity in vitro and exhibit good dose-dependency. The agonist activity of anti-OX40 21 # VHnew-L80 mAb and anti-OX40 21 # H96-L80 mAb with improved affinity is increased approximately two times.

Embodiment 8 Effects of Different Subtypes on Antibody Agonist Activity

Various variants of anti-OX40 21 # mAb have a high affinity for hOX40 and good binding kinetics to hOX40. The agonist activity of one of them, anti-OX40 21 # H96-L80 mAb is increased approximately two times. Therefore, the present application is further illustrated by taking the anti-OX40 21 # H96-L80 mAb (hereinafter referred to as H96-L80) as an example, and the rest of the variants will not be described in detail. However, it should be noted that in the following embodiments, although only H96-L80 is described, it should not be understood that the other variants of anti-OX40 21 # mAb do not have the corresponding characteristics, or the other two antibodies (O3 mAb and O19 mAb) do not have the corresponding characteristics. Further experimental data for H96-L80 in each of the following embodiments are only intended to demonstrate that the various anti-OX40 antibodies obtained according to the methods of the present invention have high activity, affinity, functionality, or stability.

Figure 8:
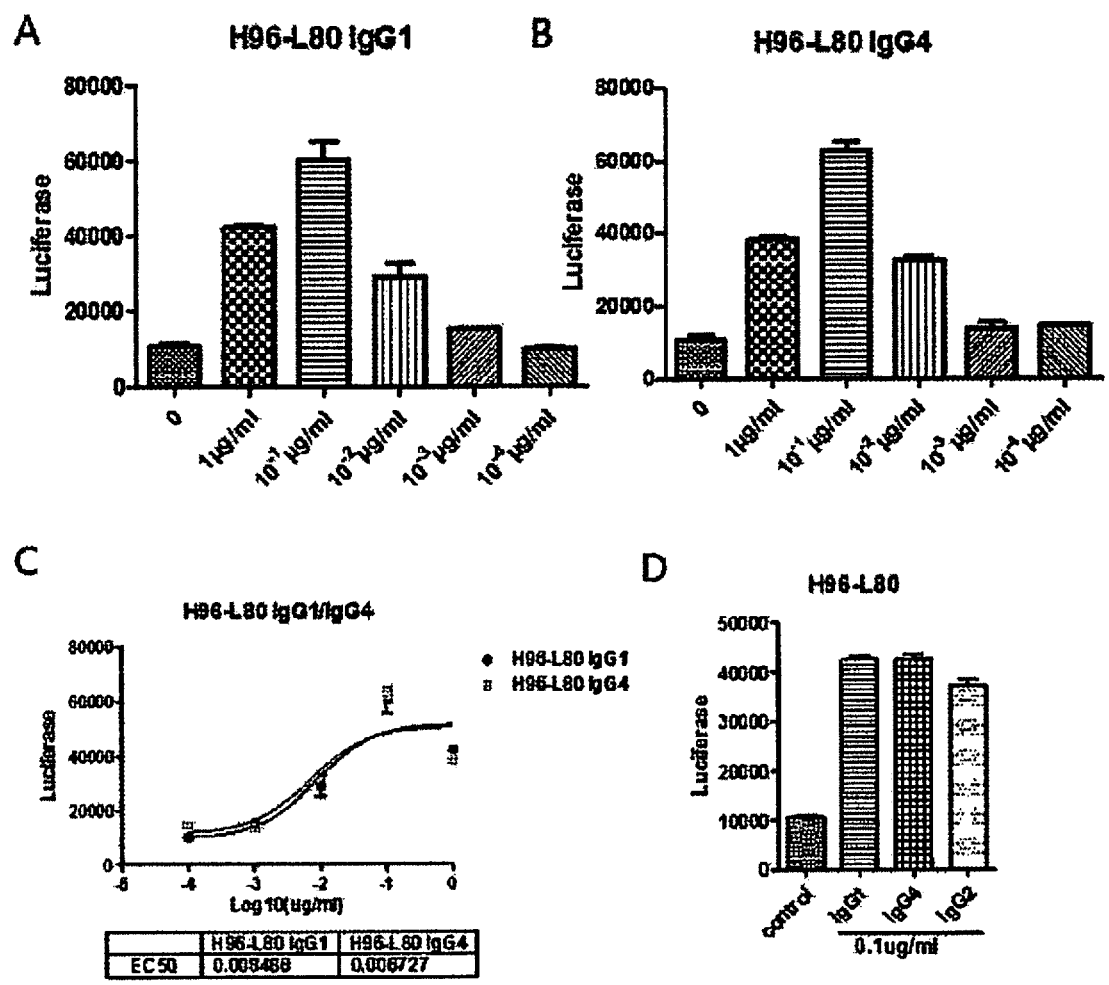
FIG. 8 is a graph comparing the in vitro agonist activity of three IgG subtypes of H96-L80.

The amino acid sequences of human IgG1 and IgG2 constant regions were obtained based on the amino acid sequences of the constant regions of human immunoglobulin gamma1 (IgG1) and human immunoglobulin gamma2 (IgG2) (P01857 and P01859 respectively) in the Uniprot protein database. The rest steps were performed as described above to give anti-OX40 21#H96-L80 IgG1 mAb and anti-OX4021#H96-L80 IgG2 mAb. The experiment was carried out according to the method in Embodiment 7, and the results are shown in FIG. 8, in which FIG. 8A and FIG. 8B show the results of in vitro agonist activity detection at different concentrations for IgG1 and IgG4 subtypes respectively; FIG. 8C shows the comparison of IgG1 and IgG4 subtypes after logistic transformation; FIG. 8D shows that the antibody agonist activities of the three subtypes of H96-L80 are comparable at 0.1 μg/ml.

Figure 9:
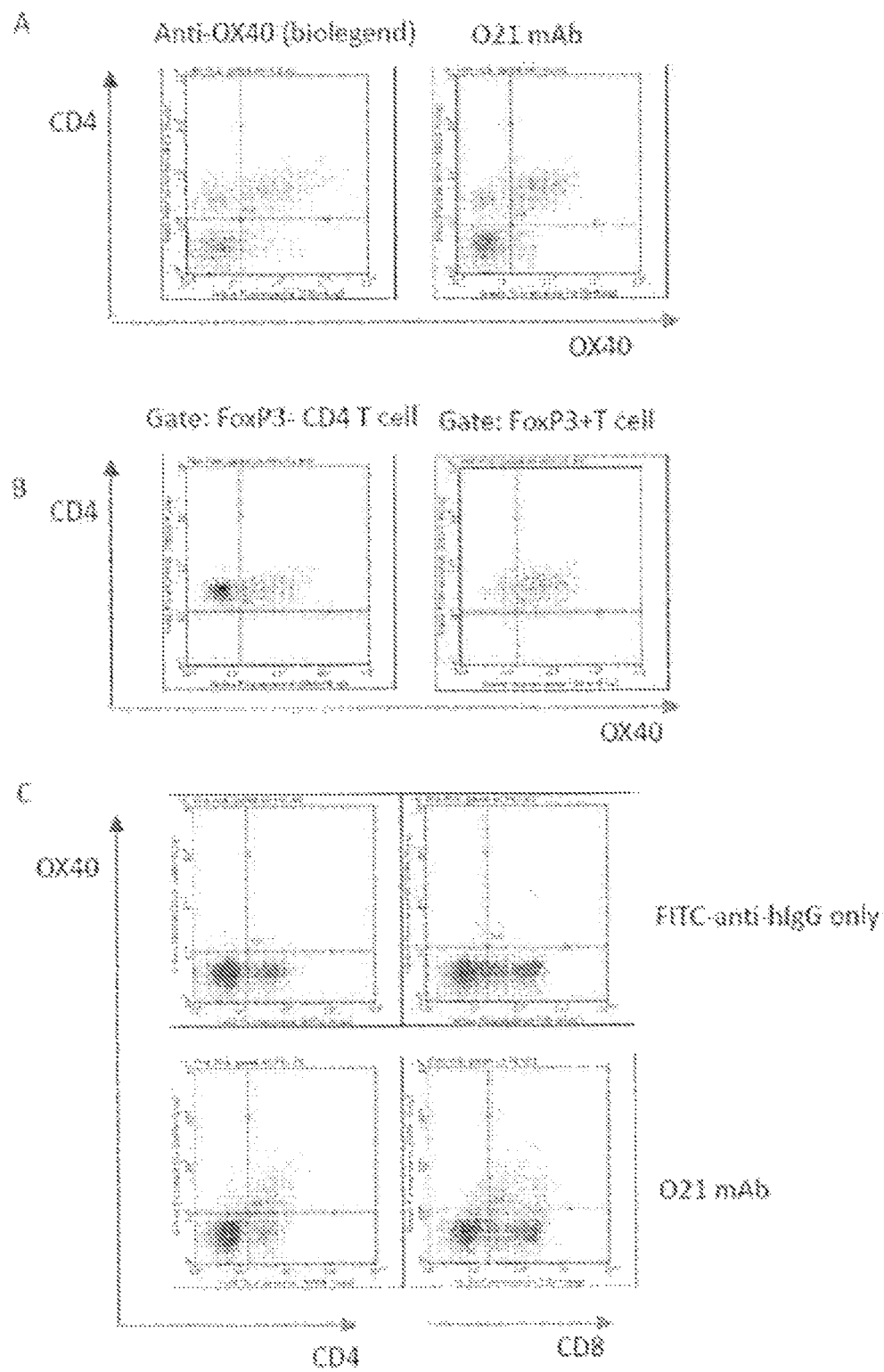
FIG. 9 is a graph showing the binding capacity of anti-OX40 antibodies to CD4+ T and CD8+ T cells in humans and macaques.

Embodiment 9: Detection of Binding Ability of Purified 1196-L80 Antibodies to CD4+T and CD8+T Cells after Activation of Human and Rhesus Peripheral blood mononuclear cells (PBMCs) were isolated from peripheral blood leukocytes of healthy donors by density gradient centrifugation using human lymphocyte separation fluid (Tianjin Hao Yang) and seeded into RPMI complete medium. PBMCs were activated with PHA at a final concentration of 5 μg/ml for 48 hours. The cells were resuspended in 0.5% PBS-BSA Buffer, H96-L80 proteins were added and the mixture was incubated on ice for 20 min. After washing, secondary antibody FITC anti-hIgG (Cat #409310) or antibody PE anti-hOX40 (Cat #350003) and antibody APC anti-human CD4 (Cat #317416) from Biolegend were added and incubated on ice for 20 min. After washing, the cells were resuspended in 500 μl of 0.5% PBS-BSA Buffer and detected by flow cytometry. Results are shown in FIG. 9A, H96-L80 binds well to activated CD4+T cells.

To test the binding ability of H96-L80 to Tregs and Teff in CD4+cells, the activated human PBMCs above were stained. The cells were resuspended in 0.5% PBS-BSA Buffer, H96-L80 proteins were added and the mixture was incubated on ice for 20 min. After washing, secondary antibody FITC anti-hIgG and antibody APC anti-human CD4 from Biolegend were added and the obtained mixture was incubated on ice for 20 min. After washing, the transmembrane fixative (BD, 51-2090 KZ) was applied for 1 h and the obtained mixture was washed using transmembrane solution (eBioscience, 00-8333-56) and then resuspended in transmembrane solution. PE anti-human Foxp3 (Cat #320208) was added and stained overnight at 4° C. After washing, the cells were resuspended in 500 μl of 0.5% PBS-BSA Buffer and detected by flow cytometry. Results are shown in FIG. 9B, H96-L80 binds well to activated CD4+Foxp3+Treg and CD4+Foxp3−Teff cells.

To test the binding ability of H96-L80 to rhesus OX40, activated rhesus peripheral blood mononuclear cells were obtained using the above procedure. The cells were resuspended in 0.5% PBS-BSA Buffer, H96-L80 proteins were added and the mixture was incubated on ice for 20 min. After washing, secondary antibody FITC anti-hIgG or antibody APC anti-human CD4 and PE anti-human CD8a (Cat#301008) from Biolegend were added and incubated on ice for 20 min. After washing, the cells were resuspended in 500 μl of 0.5% PBS-BSA Buffer and detected by flow cytometry. Results are shown in FIG. 9C, H96-L80 well binds to activated rhesus CD4+T and CD8+T cells, suggesting that H96-L80 can bind to rhesus OX40.

Embodiment 10: Anti-OX40 Antibody Promotes Activation and Proliferation of T Cells 10.1 The activation and proliferation of T-cells were used to study the in vitro activity of anti-OX40 scFv antibodies and evaluate their agonist function.

Figure 10:
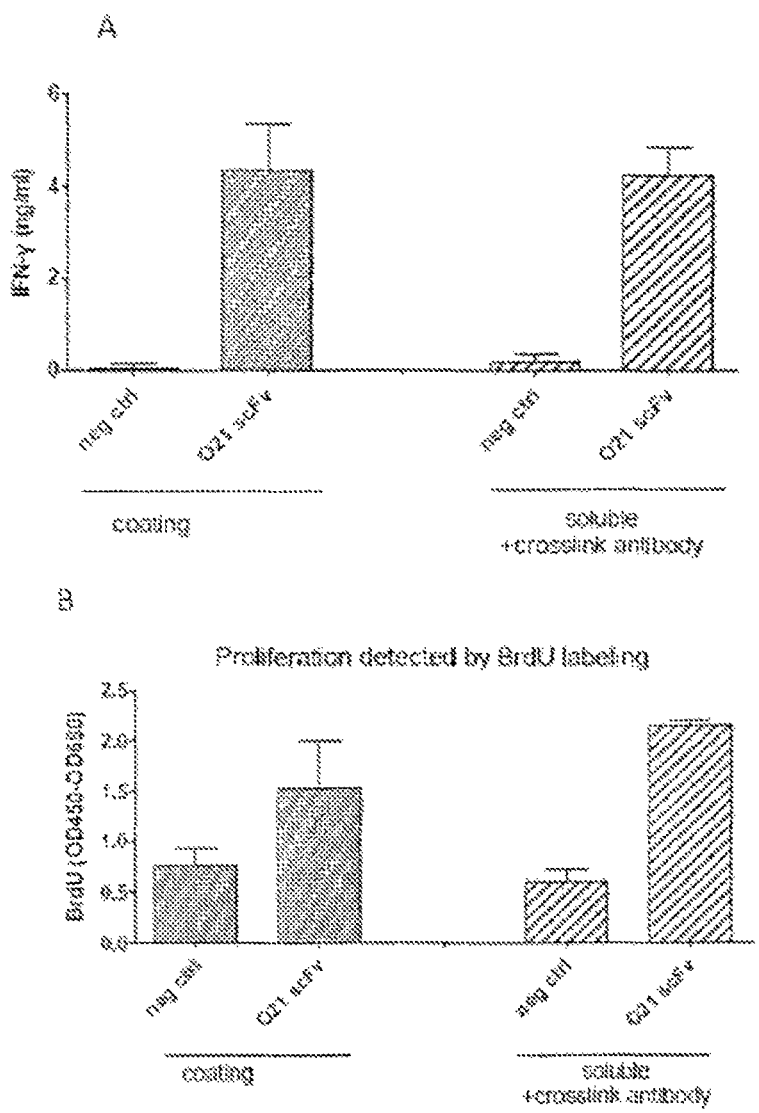
FIG. 10 is a graph showing the results of activity detection of O21 scFv antibody agonist.

Peripheral blood mononuclear cells (PBMCs) were isolated from peripheral blood leukocytes of healthy donors by density gradient centrifugation using human lymphocyte separation fluid (Tianjin Hao Yang) and seeded into RPMI complete medium. 96-well plates were pre-coated with 50 μl of 1 μg/ml anti-CD3 overnight at 4° C. The plates in the experimental group was coated with 50 μl of 2 μg/ml O21 scFv at 37° C. for 2 h, at the same time, soluble O21 scFv with a final concentration of 2 μg/ml and cross-link (Jackson ImmunoResearch Laboratories: 109-006-008) with a final concentration of 4 μg/ml were added. The negative control was RPMI complete medium. The amount of PBMCs was $2\times10^5$/well, the cells were cultured for five days and then the supernatant was taken. As shown in FIG. 10, the level of IFN-γ in the supernatant was detected by the IFN-γ ELISA detection kit (FIG. 10A) and the proliferation of T cells was detected by the BrdU staining kit (Roche: 11647229001). It can be seen that O21 scFv has good activity of activating PBMCs and promoting the proliferation of T cells under both coating and cross-link administration modes.

10.2 the Agonist Activities of O21 scFv and IgG were Assessed Through In Vitro Activation of PBMCs and CD4+T Cells Peripheral blood mononuclear cells (PBMCs) were isolated from peripheral blood leukocytes of healthy donors by density gradient centrifugation using human lymphocyte separation fluid (Tianjin Hao Yang) and seeded into RPMI complete medium. CD4+T cells were isolated from PBMCs using CD4+T Cell Isolation Kit (Miltenyi, cat # no. 130-096-533). 96-well plates were pre-coated with 50 μl of 1 μg/ml anti-CD3 overnight at 4° C. The plates in the experimental group was coated with 50 μl of 2 μg/ml O21 scFv or O21 mAb at 37° C. for 2 h and the negative control was the same dose of hIgG-Fc. The amount of PBMCs and CD4+T cells was $2 \times 10^5$/well, and the supernatant was collected after five days of culture. The level of IFN-γ in the supernatant was detected by IFN-γ ELISA kit (ebioscience).

Figure 11:
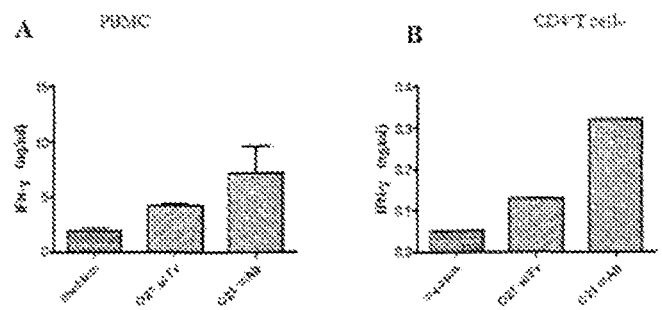
FIG. 11 shows the results of activity detection of O21 scFv and IgG agonists.

As shown in FIG. 11, it can be seen that O21 mAb has better agonist activity than O21 scFv for PBMCs (FIG. 11A) and CD4+T cells (FIG. 11B).

Figure 12:
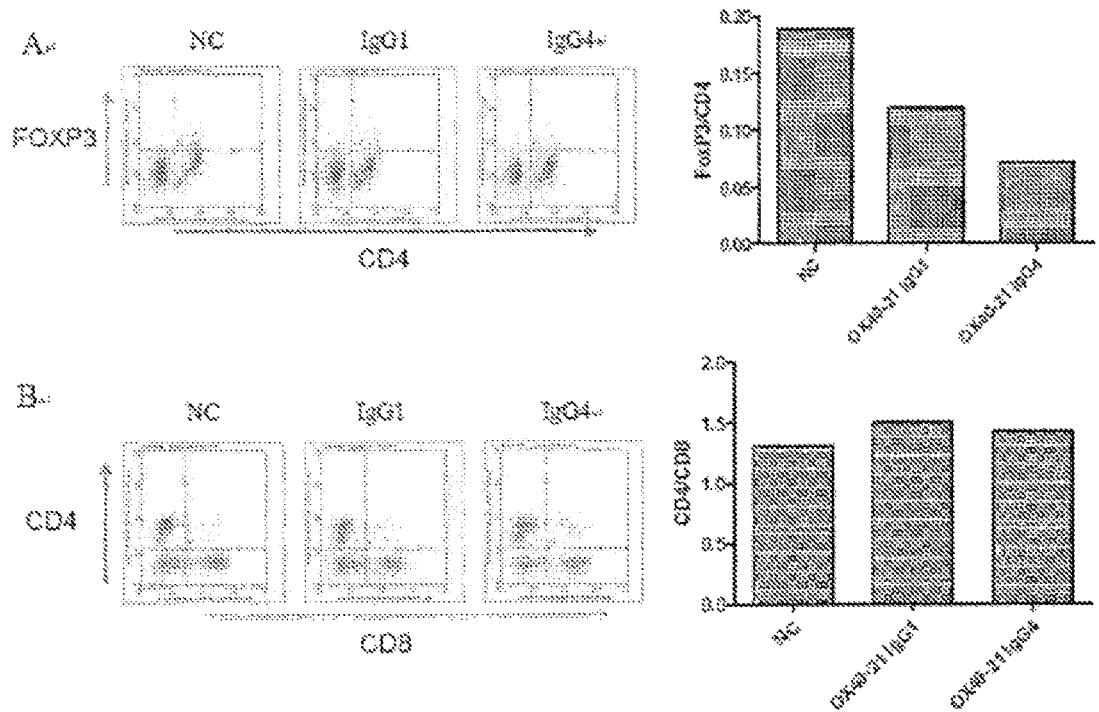
FIG. 12 shows the in vitro effect of IgG1 and IgG4 subtypes of H96-L80 on T cell subtypes.

Embodiment 11: Effect of IgG1 and IgG4 Subtypes of Anti-OX40 Antibody H96-L80 on T-Cell Subsets Human peripheral blood mononuclear cells (PBMCs) were obtained according to Embodiment 10 and PBMCs were stimulated with dissolved anti-CD28 (0.5 μg/ml) and plate-bound anti-CD3 (3 μg/ml), and anti-human OX40 mAb H96-L80 IgG1 or IgG4 (10 μg/ml). After 48 hours, the cells were harvested. The cells were stained with antibody APC anti-human CD4 and PE anti-human CD8a (Cat #301008) from Biolegend or stained with antibody APC anti-human CD4 and PE anti-human Foxp3 (Cat #320208) from Biolegend, and then detected by flow cytometry. Results are shown in the figure below. Both the O21 mAb H96-L80 IgG1 and IgG4 subtypes reduce the proportion of CD4+Foxp3+Tregs in CD4+T cells (FIG. 12A) but do not affect the ratio of CD4+T to CD8+T cells (FIG. 12B).

Figure 13:
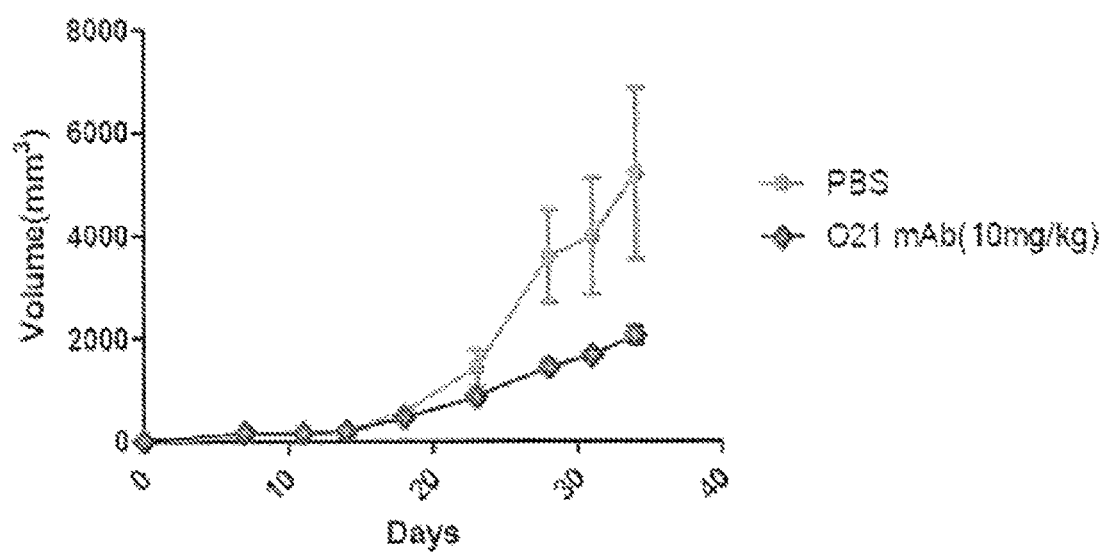
FIG. 13 is a graph showing the in vivo growth inhibition effect of O21 mAb on a tumor (PC-3)

Embodiment 12: Inhibition of Tumor Growth by Anti-OX40 Antibody in Mice 12.1 the NOD-SCID Mouse Tumor Model Implanted with Tumor Cells PC-3 and Human PBMCs was Used to Evaluate the In Vivo Efficacy of Anti-OX40 Antibody Mice were injected subcutaneously (SC) with PC-3 (ATCC CRL-1435™) and human peripheral blood mononuclear cells (PBMCs) on day 0 and injected intraperitoneally with 10 mg/kg O21 mAb or PBS on days 0 and 7, PBS was used as a negative control, each group comprised 5 mice. Tumor formation was observed twice a week and the major and minor diameters of the tumors were measured with a vernier caliper. The tumor volume was calculated, and the tumor growth curve was plotted. The results are shown in FIG. 13, and it can be seen that the antibody O21 mAb can significantly inhibit tumor growth.

Figure 14:
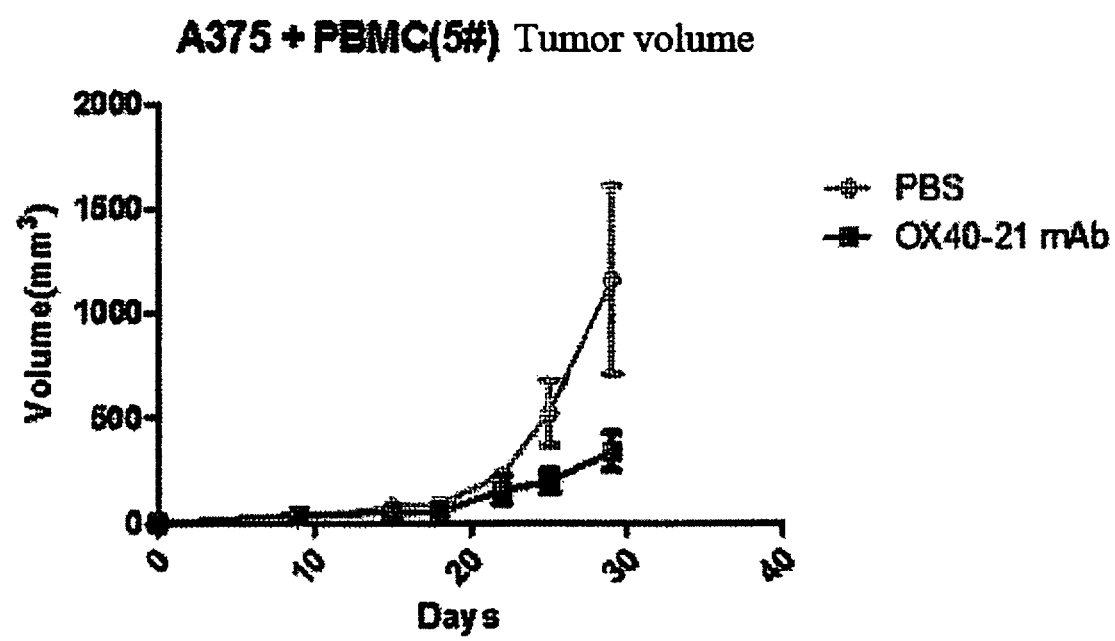
FIG. 14 is a graph showing the in vivo growth inhibition effect of O21 mAb on a tumor (A375)

12.2 the NOD-SCID Mouse Tumor Model Implanted with Tumor Cells A375 and Human PBMCs was Used to Evaluate the In Vivo Efficacy of Anti-OX40 Antibody Mice were injected subcutaneously (SC) with $7 \times 10^6$ of A375 (ATCC CRL-1619™) and $1 \times 10^6$ of human peripheral blood mononuclear cells (PBMCs) on Day 0 and injected intraperitoneally with 1 mg/kg O21 mAb or PBS on Day 0 and Day 7, PBS was used as a negative control, each group comprised 5 mice. Tumor formation was observed twice a week and the major and minor diameters of the tumors were measured with a vernier caliper. The tumor volume was calculated, and the tumor growth curve was plotted. It can be seen in FIG. 14 that the antibody O21 mAb can significantly inhibit tumor growth.

Embodiment 13: Stability Test of Anti-OX40 Abs

Figure 15:
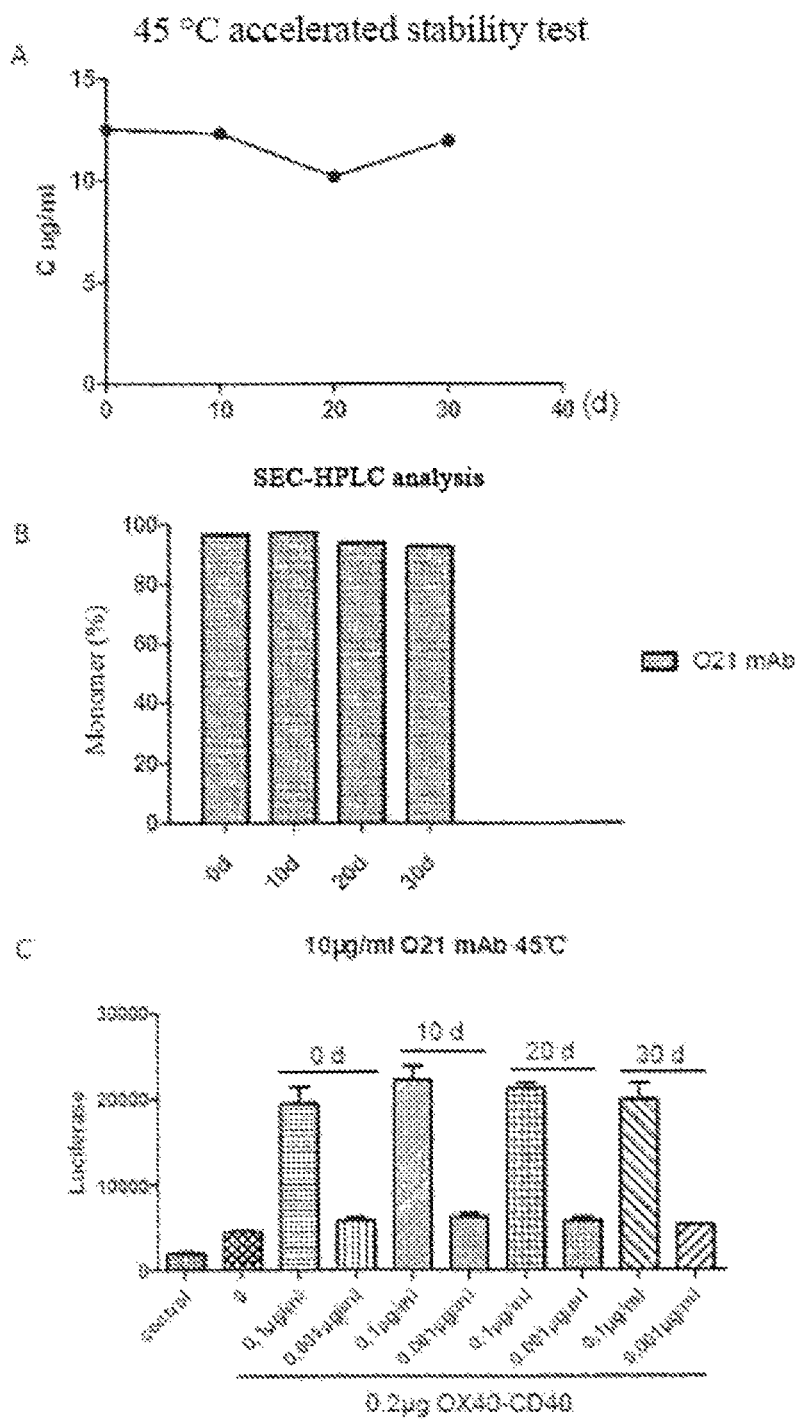
FIG. 15 is a graph showing the stability of anti-OX40 antibodies evaluated by a 45° C. accelerated stability test, Where A is concentration measurement, B is monomer content measurement, C is in vitro activity detection using an NF-κb system.

The stability of the anti-hOX40 antibody O21 mAb was tested using an accelerated stability test at 45° C. The specific experimental method is as follows: the anti-O21 mAb antibody was concentrated to about 10 mg/ml, placed in a 45° C. water bath, and sampled on Day 0, Day 10, Day 20 and Day 30 for concentration, SEC-HPLC and NF-κb analysis experiment. SEC-HPLC analysis experiment was performed using Shimadzu LC20ATHPLC liquid chromatograph; the sample was concentrated to 1 mg/ml, the flow rate was 0.5 ml/min, the total sample volume was 50 μg; after sample loading, isocratic elution was performed for 30 min; NF-κb analysis experiment was performed as in Embodiment 7, and the results are shown in FIG. 15, it can be seen that anti-hOX40 antibody O21 mAb has good stability in vitro.

Embodiment 14 Pharmacokinetic Evaluation of Anti-hOX40 Antibody O21 mAb

Figure 16:
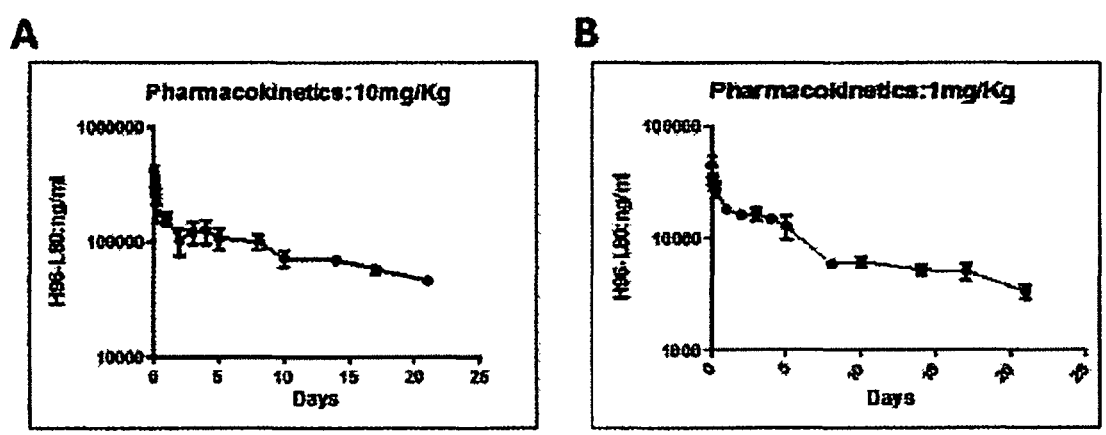
FIG. 16 shows the pharmacokinetic results of the H96-L80 antibody.

The pharmacokinetics of the H96-L80 IgG1 antibody was evaluated at a dose of 10 mg/kg and 1 mg/kg. Balb/C mice (female, 8-week-old) were used, 16 mice were selected, and each dose was divided into A/B groups, with each group comprising four mice. All the mice were injected intravenously with 200 μg (10 mg/kg) or 20 μg (1 mg/kg) of the H96-L80 IgG1 antibody. After administration, 100 μl of blood was taken at 14 points in time respectively. One group of mice was taken at each time point, two groups took turns. Serum was separated. The concentration of the test protein in serum was determined by ELISA: plates were coated with hOX40-muFc, serum samples with appropriate degree of dilution were added and Goat anti-Human IgG HRP (Sigma Cat NO: A0170) was added and color development test was performed using TMB. H96-L80 IgG1 antibody was used as a standard protein for making a standard curve. Pharmacokinetic parameters were calculated using WinNolin software. The mean C-T curve is shown in FIG. 16. The H96-L80 IgG1 antibody of the present invention is relatively stable. The half-life in vivo thereof averages 205 hours at a dose of 1 mg/kg and the half-life in vivo thereof averages 371 hours at a dose of 10 mg/kg. After detection, there are no production of antibodies against anti-H96-L80 antibody.

The above is only the preferred embodiments of the present invention and is not intended to limit the present invention. It should be noted that those skilled in the art can make various improvements and variations without departing from the technical principles of the present invention, these improvements and variations shall also be regarded as falling within the protection scope of the present invention.

What is claimed is:

1. An anti-OX40 antibody or an antigen-binding part thereof, comprising a group of CDRs selected from the following groups:
   1) a heavy chain variable region CDR1, CDR2 and CDR3 having a sequence as set forth in SEQ ID NO: 5-7 respectively, a light chain variable region CDR1, CDR2 and CDR3 having a sequence as set forth in SEQ ID NO: 14-16 respectively;
   2) a heavy chain variable region CDR1, CDR2 and CDR3 having a sequence as set forth in SEQ ID NO: 23-25 respectively, a light chain variable region CDR1, CDR2 and CDR3 having a sequence as set forth in SEQ ID NO: 32-34 respectively;
   3) a heavy chain variable region CDR1, CDR2 and CDR3 having a sequence as set forth in SEQ ID NO: 41-43 respectively, a light chain variable region CDR1, CDR2 and CDR3 having a sequence as set forth in SEQ ID NO: 50-52 respectively;
   4) a heavy chain variable region CDR1, CDR2 and CDR3 as set forth in SEQ ID NO: 63, 42, 43 respectively, a light chain variable region CDR1, CDR2 and CDR3 as set forth in SEQ ID NO: 50-52 respectively;
   5) a heavy chain variable region CDR1, CDR2 and CDR3 as set forth in SEQ ID NO: 41, 67, 43 respectively, a light chain variable region CDR1, CDR2 and CDR3 as set forth in SEQ ID NO: 50-52 respectively;
   6) a heavy chain variable region CDR1, CDR2 and CDR3 as set forth in SEQ ID NO: 41, 42, 70 respectively, a light chain variable region CDR1, CDR2 and CDR3 as set forth in SEQ ID NO: 50-52 respectively;
   7) a heavy chain variable region CDR1, CDR2 and CDR3 as set forth in SEQ ID NO: 63, 67, 70 respectively, a light chain variable region CDR1, CDR2 and CDR3 as set forth in SEQ ID NO: 75-77 respectively, and
   8) a heavy chain variable region CDR1, CDR2 and CDR3 as set forth in SEQ ID NO: 41, 42, 70 respectively, a light chain variable region CDR1, CDR2 and CDR3 as set forth in SEQ ID NO: 75-77 respectively.

2. The anti-OX40 antibody or the antigen-binding part thereof according to, claim 1, comprising a heavy chain variable region having a sequence selected from the group consisting of SEQ ID NO: 4, 22, 40, 62, 66, 69, 72 and 79.

3. The anti-OX40 antibody or the antigen-binding part thereof according to, claim 1, comprising a light chain variable region having a sequence selected from the group consisting of SEQ ID NO: 13, 31, 49 and 74.

4. A conjugate, comprising the anti-OX40 antibody or the antigen-binding part thereof according to claim 1, and an additional bioactive substance, wherein the anti-OX40 antibody or the antigen-binding part thereof is conjugated, either directly or through a linker, to the additional bioactive substance.

5. A composition, comprising the anti-OX40 antibody or antigen-binding part thereof according to claim 1, and optionally a pharmaceutically acceptable carrier or excipient.

6. A method for treating a tumor in a subject, comprising administering to said subject a therapeutically effective amount of the anti-OX40 antibody or the antigen-binding part thereof according to claim 1.

* * * * *